US012533434B2

(12) United States Patent
Brown

(10) Patent No.: US 12,533,434 B2
(45) Date of Patent: Jan. 27, 2026

(54) SANITIZING DEVICES AND METHODS

(71) Applicant: FUSE, LLC, Memphis, TN (US)

(72) Inventor: Matthew S. Brown, Falkner, MS (US)

(73) Assignee: FUSE, LLC, Memphis, TN (US)

( * ) Notice: Subject to any disclaimer, the term of this patent is extended or adjusted under 35 U.S.C. 154(b) by 543 days.

(21) Appl. No.: 17/981,047

(22) Filed: Nov. 4, 2022

(65) Prior Publication Data

US 2023/0055756 A1 Feb. 23, 2023

Related U.S. Application Data

(63) Continuation of application No. PCT/US2021/031295, filed on May 7, 2021.

(60) Provisional application No. 63/056,207, filed on Jul. 24, 2020, provisional application No. 63/021,148, filed on May 7, 2020.

(51) Int. Cl.
*A61L 2/10* (2006.01)
*A61L 2/26* (2006.01)

(52) U.S. Cl.
CPC .................. *A61L 2/10* (2013.01); *A61L 2/26* (2013.01); *A61L 2202/11* (2013.01); *A61L 2202/122* (2013.01); *A61L 2202/16* (2013.01)

(58) Field of Classification Search
CPC .............. B65D 51/248; A47G 23/0216; A47G 19/2227; A47G 23/0241; A47G 23/0266; A47G 2019/2238; A47G 2023/0219; A47G 2200/18; G09D 13/00; G09D 23/0091; G09D 23/04; G09D 9/33; G09D 2013/222; G02B 6/0005
USPC .......................................... 206/457; 220/737
See application file for complete search history.

(56) References Cited

U.S. PATENT DOCUMENTS

| | | | |
|---|---|---|---|
| 3,500,014 | A | 3/1970 | Longo |
| 3,949,258 | A | 4/1976 | Soodak |
| 3,982,130 | A | 9/1976 | Trumble |
| 4,241,282 | A | 12/1980 | Tresch et al. |

(Continued)

FOREIGN PATENT DOCUMENTS

| | | |
|---|---|---|
| CH | 670150 | 5/1989 |
| FR | 285103 | 1/2006 |

(Continued)

OTHER PUBLICATIONS

European Patent Office, English translation of KR20120120662A, Sep. 9, 2024.

(Continued)

*Primary Examiner* — Chun Hoi Cheung
(74) *Attorney, Agent, or Firm* — ASHLEY LAW FIRM P.C.; Stephen S. Ashley, Jr.

(57) ABSTRACT

A container apparatus includes an enclosure and a light assembly. The enclosure defines an interior area for storing items therein, and has an interior surface facing the interior area and at least one substantially concave recess formed in the interior surface forming a recessed portion of the interior surface. The substantially concave recess can be sized and shaped to receive and releasably retain the light assembly therein. The light assembly comprises a light emitting device and can be substantially flush with a non-recessed portion of the interior surface when positioned in the substantially concave recess. The light emitting device emits ultraviolet light having a wavelength of 100 to 280 nanometers.

19 Claims, 28 Drawing Sheets

(56) References Cited

U.S. PATENT DOCUMENTS

| | | | | |
|---|---|---|---|---|
| 4,422,824 | A | 12/1983 | Eisenhardt, Jr. | |
| 4,754,376 | A | 6/1988 | Winslow | |
| 4,984,760 | A | 1/1991 | Cohn et al. | |
| 5,067,771 | A | 11/1991 | Ellis | |
| 5,121,307 | A | 6/1992 | Moore | |
| 5,178,450 | A | 1/1993 | Zelensky | |
| 5,497,207 | A | 3/1996 | Kim | |
| 5,613,756 | A | 3/1997 | Allen | |
| 5,750,962 | A | 5/1998 | Hyatt | |
| 5,768,898 | A | 6/1998 | Seok et al. | |
| 6,182,462 | B1 | 2/2001 | Bania et al. | |
| 6,283,612 | B1 | 9/2001 | Hunter | |
| 6,769,773 | B1 | 8/2004 | Wu | |
| 6,773,682 | B1 | 8/2004 | Benda | |
| 6,911,657 | B2 | 6/2005 | Waluszko | |
| 6,924,495 | B1 | 8/2005 | Brickley | |
| 6,997,007 | B1 | 2/2006 | Wyatt | |
| 7,162,890 | B2 | 1/2007 | Mogil et al. | |
| 7,226,170 | B2 | 6/2007 | Hsu | |
| 7,428,823 | B2 | 9/2008 | Reinders | |
| 7,763,212 | B2 | 7/2010 | McEllen | |
| 7,984,997 | B1 | 7/2011 | Sandberg | |
| 8,080,203 | B2 | 12/2011 | First et al. | |
| 8,096,442 | B2 | 1/2012 | Ramundi | |
| 8,193,515 | B2 * | 6/2012 | Kreitenberg | A63B 47/04 250/455.11 |
| 8,210,702 | B1 | 7/2012 | Sandberg | |
| 8,511,846 | B1 | 8/2013 | Sandberg | |
| 8,590,726 | B1 | 11/2013 | Mickelson et al. | |
| 8,844,316 | B1 | 9/2014 | Ademola et al. | |
| 8,888,086 | B2 * | 11/2014 | Rastegar | G03F 7/70916 269/903 |
| 9,027,806 | B1 | 5/2015 | Giogga | |
| 9,044,521 | B2 | 6/2015 | Farren | |
| 9,255,673 | B2 | 2/2016 | Horn | |
| 9,303,912 | B1 | 4/2016 | Schalla et al. | |
| 9,463,890 | B2 | 10/2016 | Mowry | |
| 9,546,677 | B2 | 1/2017 | Wicks | |
| 9,568,186 | B2 | 2/2017 | Brown | |
| 9,671,158 | B1 | 6/2017 | Sandberg et al. | |
| 9,706,831 | B2 | 7/2017 | Wu | |
| 9,726,424 | B1 | 8/2017 | Sandberg | |
| 9,728,058 | B2 | 8/2017 | Ku et al. | |
| 9,890,993 | B1 | 2/2018 | Sandberg | |
| 9,975,675 | B1 | 5/2018 | Kuo | |
| 10,001,321 | B2 | 6/2018 | Statham | |
| 10,082,329 | B1 | 9/2018 | Sandberg et al. | |
| 10,088,144 | B1 | 10/2018 | Sandberg | |
| 10,337,701 | B2 | 7/2019 | Mastenbroek et al. | |
| 10,490,048 | B2 | 11/2019 | Stibich et al. | |
| 10,688,210 | B2 | 6/2020 | Shatalov et al. | |
| 10,871,279 | B1 | 12/2020 | Lu et al. | |
| 10,874,233 | B2 | 12/2020 | Santiago | |
| 10,931,156 | B2 | 2/2021 | Chen et al. | |
| 10,996,488 | B2 | 5/2021 | Brown | |
| 11,035,567 | B2 | 6/2021 | Brown | |
| 11,383,903 | B1 | 7/2022 | Gayle | |
| 11,666,179 | B2 | 6/2023 | Mogil et al. | |
| 2002/0008841 | A1 | 1/2002 | Ohmuro | |
| 2003/0081408 | A1 | 5/2003 | Tai | |
| 2004/0047776 | A1 | 3/2004 | Thomsen | |
| 2004/0175288 | A1 | 9/2004 | Horton, III | |
| 2005/0047118 | A1 | 3/2005 | Spahr et al. | |
| 2005/0213326 | A1 | 9/2005 | Sanford | |
| 2006/0196218 | A1 | 9/2006 | Mogil | |
| 2007/0103895 | A1 | 5/2007 | Riesebosch | |
| 2007/0206372 | A1 | 9/2007 | Casillas | |
| 2009/0004046 | A1 | 1/2009 | McEllen | |
| 2009/0008402 | A1 * | 1/2009 | Lau | B65F 7/00 220/23.9 |
| 2009/0175029 | A1 | 7/2009 | Chiang | |
| 2013/0104579 | A1 | 5/2013 | Zhou | |
| 2014/0043837 | A1 | 2/2014 | Michaud | |
| 2014/0204565 | A1 | 7/2014 | Zwierstra | |
| 2015/0069096 | A1 | 3/2015 | Kampas | |
| 2016/0018070 | A1 | 1/2016 | Van Deursen et al. | |
| 2018/0020814 | A1 | 1/2018 | Pasinski | |
| 2018/0201432 | A1 | 7/2018 | Harding | |
| 2020/0003487 | A1 | 1/2020 | Brown | |
| 2020/0100513 | A1 | 4/2020 | Young | |
| 2021/0322602 | A1 * | 10/2021 | Furia | A61L 2/10 |
| 2022/0214035 | A1 | 7/2022 | Brown | |
| 2022/0282911 | A1 | 9/2022 | Brown | |
| 2022/0364712 | A1 | 11/2022 | Brown | |
| 2023/0200575 | A1 | 6/2023 | Brown | |
| 2023/0235939 | A1 | 7/2023 | Brown | |

FOREIGN PATENT DOCUMENTS

| | | | |
|---|---|---|---|
| KR | 20120120662 | A | 11/2012 |
| RU | 2026084 | C1 | 1/1995 |
| RU | 42623 | U1 | 12/2004 |
| RU | 44508 | U1 | 3/2005 |
| RU | 54138 | U1 | 6/2006 |
| RU | 73595 | U1 | 5/2008 |
| RU | 78632 | U1 | 12/2008 |
| RU | 81557 | U1 | 3/2009 |
| RU | 117575 | U1 | 6/2012 |
| RU | 2505735 | C1 | 1/2014 |
| RU | 2714623 | C2 | 2/2020 |
| SU | 810091 | A3 | 2/1981 |
| WO | WO2015176960 | A1 | 11/2015 |

OTHER PUBLICATIONS

Fish & Richardson P.C., "Claim Charts—U.S. Appl. No. 18/129,608", filed Sep. 15, 2024.
Fish & Richardson P.C., "Claim Charts—U.S. Appl. No. 18/430,002", filed Sep. 15, 2024.
patents.google.com, English translation of RU78632U1, accessed Dec. 13, 2021.
patents.google.com, English translation of RU54138U1, accessed Dec. 13, 2021.
patents.google.com, English translation of RU2505735C1, accessed Dec. 3, 2021.
patents.google.com, English translation of RU2026084C1, accessed Dec. 3, 2021.
patents.google.com, English translation of RU81557U1, accessed Dec. 3, 2021.
patents.google.com, English translation of RU117575U1, accessed Dec. 3, 2021.
patents.google.com, English translation of RU44508U1, accessed Dec. 3, 2021.
patents.google.com, English translation of RU42623U1, accessed Dec. 3, 2021.
patents.google.com, English translation of RU73595U1, accessed Dec. 3, 2021.
patents.google.com, English translation of RU2714623C2, accessed Dec. 13, 2021.
patents.google.com, English translation of SU810091A3, accessed Dec. 13, 2021.
patents.google.com, English translation of FR2851034, accessed Aug. 31, 2023.
patents.google.com, English translation of CH670150, accessed Aug. 31, 2023.

* cited by examiner

SANITIZING DEVICES AND METHODS

CROSS REFERENCE TO RELATED APPLICATIONS

This application is a continuation of International Application No. PCT/US2021/031295, filed May 7, 2021, which claims priority to U.S. Provisional Patent Application No. 63/021,148 filed May 7, 2020, and U.S. Provisional Patent Application No. 63/056,207 filed Jul. 24, 2020. All of said applications are incorporated herein by reference. In addition, U.S. Pat. No. 10,514,164, U.S. Patent Application Publication No. 2020/0003487, International Patent Publication No. Wo2019/084542A1, U.S. Provisional Patent Application No. 62/895,718, filed Sep. 4, 2019, titled "ILLUMINATION APPARATUS, ATTACHMENT APPARATUS AND METHODS OF USING SAME", and U.S. Provisional Patent Application No. 61/204,016, filed Jan. 2, 2009, titled "LIGHTED ENCLOSURE ASSEMBLY", are incorporated herein by reference.

TECHNICAL FIELD

The present invention relates to devices and methods for reducing and/or eliminating pathogenic agents, such as viruses, bacteria and fungi. One embodiment of the invention comprises an insulated cooler that is adapted to receive a removable germicidal lighting emitting device. The light emitting device can be secured in the cooler so that it does not move during use and can be easily removed from the cooler when desired.

BACKGROUND

When using a container, such as an insulated cooler, the user may desire a light to emit light in the interior of the container. For example, such a light can aid the user in getting a certain food item contained in a cooler. Attempts have been made in the prior art to address this need. However, many such prior art devices comprise containers in which lights are electrically wired to the container itself. Such a system can be relatively expensive, and if the lights fail it is generally difficult and impractical to repair. Also, it can be relatively difficult to replace batteries in such containers. In addition, the Coronavirus disease 2019 (COVID-19) pandemic has been a public health crises, and there continues to be a need for devices that can conveniently and effectively deactivate viruses and bacteria.

SUMMARY

One object of the present invention is to provide an apparatus comprising means for deactivating viruses and bacteria. Another object of the invention is to provide a container apparatus that can receive and engage an assembly for illuminating the interior of the container. Yet another object of the invention is to provide a container apparatus having an interior lighting assembly that can be easily removed from the container when desired. Yet another object of the invention is to provide a container apparatus comprising means for deactivating viruses and bacteria on items within the interior of the container apparatus. These and other objects of the present invention can be achieved in various embodiments of the invention described herein.

One embodiment of the invention comprises a container apparatus comprising an enclosure and means for deactivating viruses, bacteria, and other pathogens within the enclosure.

According to an embodiment of the invention, the means for deactivating viruses, bacteria, and other pathogens within the enclosure comprises an ultraviolet light emitting device.

According to another embodiment of the invention, the container apparatus can be a hard case container, thermally insulated cooler, backpack, lunch box, medical bag, luggage bag, gear bag, grocery bag, beach bag and/or toolbox.

Another embodiment of the invention comprises a container apparatus comprising an enclosure and a light emitting device. At least one substantially concave recess is formed in the interior surface of the enclosure and is sized and shaped to receive and engage the light emitting device therein.

According to another embodiment of the invention, the light emitting device emits short wave (UV-C) ultraviolet light.

Another embodiment of the invention comprises a container apparatus comprising an enclosure and an insert assembly, the enclosure defining an interior area for storing items therein. The enclosure has an interior surface facing the interior area and at least one substantially concave recess formed in the interior surface to form a recessed portion of the interior surface. The substantially concave recess is sized and shaped to receive and frictionally engage the insert assembly, wherein the insert assembly is substantially flush with a non-recessed portion of the interior surface when positioned in the substantially concave recess.

According to an embodiment of the invention, the insert assembly comprises at least one light emitting device.

According to an embodiment of the invention, the light emitting device can emit short wave (UV-C) ultraviolet light.

According to an embodiment of the invention, the light emitting device is releasably retained within the substantially concave recess and can be slid in and out of the recess.

According to an embodiment of the invention, the light emitting device can be removed from the container apparatus without removing any other component of the container apparatus.

According to an embodiment of the invention, the light emitting device is not electrically connected to the enclosure.

According to another embodiment of the invention, the enclosure comprises a rectangular base and a rectangular sidewall extending upwardly from the base defining four corners of the enclosure, and at least one elongate recess is formed at one of the four corners defined by the sidewall.

According to another embodiment of the invention, the container apparatus includes a light assembly having at least one elongate light member, which is positioned within the elongate recess.

According to another embodiment of the invention, each elongate light member comprises a cooling or heating element. The cooling or heating element can be battery powered.

According to another embodiment of the invention, the container apparatus includes at least one elongate member positioned within the elongate recess. The elongate recess comprises a cooling or heating element. The cooling or heating element can be battery powered.

According to another embodiment of the invention, four elongate recesses are formed at the four corners defined by the sidewall.

According to another embodiment of the invention, four elongate light members are positioned within the four elongate recesses.

According to another embodiment of the invention, the rectangular sidewall comprises an outer wall section and an inner wall section, the inner wall section having an upper edge positioned below an upper edge of the outer wall section, such that the upper edge of the inner wall section defines a rest platform.

According to another embodiment of the invention, four elongate recesses are formed at the four corners of the sidewall. The elongate recesses begin at the upper edge of the inner wall section and extending downwardly to the base.

According to another embodiment of the invention, the container apparatus includes a light assembly comprising a rectangular frame having a perimeter approximately equal to a perimeter defined by the rest platform and defining four corners corresponding to the corners of the enclosure, and four elongate light members extend downwardly from the rectangular frame member. The light members are attached at the corners of the frame and are positioned within the four elongate recesses of the enclosure.

According to another embodiment of the invention, the rectangular frame of the light assembly rests on the rest platform of the enclosure.

According to another embodiment of the invention, the enclosure is a thermally insulated cooler.

According to another embodiment of the invention, the container apparatus includes a lid pivotally attached to the enclosure. The lid can be operatively connected to the light assembly, such that the light assembly emits light when the lid is opened.

According to another embodiment of the invention, the container apparatus includes a lid having a transparent or translucent section. As such, light emitting from the light assembly can be visible through the lid.

According to another embodiment of the invention, the enclosure is a toolbox.

According to another embodiment of the invention, a substantially circular shaped recess is formed in the base of the enclosure.

According to another embodiment of the invention, a light assembly comprising a circular shaped light is positioned within the circular recess. At least one attachment member is connected to a bottom surface of the light and is releasably attached to the base of the enclosure.

According to another embodiment of the invention, the attachment member is a suction cup, and a plurality of suction cups are connected to a bottom surface of the light.

Another embodiment of the invention comprises a container kit comprised of a light assembly having four elongate light members, and a container. The container can comprise a rectangular base and a rectangular sidewall extending upwardly from the base. The sidewall defines four corners of the container, and four elongate recesses are formed in the sidewall proximate the four corners of the sidewall to receive the elongate light members. The recesses are sized and shaped to conform to the elongate light members so that the light members can be releasably retained within the elongate recesses.

According to another embodiment of the invention, the rectangular sidewall comprises an outer wall section and an inner wall section. The inner wall section has an upper edge positioned below an upper edge of the outer wall section, such that the upper edge of the inner wall section defines a rest platform.

According to another embodiment of the invention, the light assembly includes a rectangular frame having a perimeter approximately equal to the perimeter of the rest platform, and has four corners corresponding to the corners of the container. The four elongate light members are attached at the four corners of the frame, and the rectangular frame rests on the rest platform of the container.

A container apparatus according to another preferred embodiment of the invention comprises an enclosure having a base and at least one sidewall extending upwardly from the base. At least one recess is formed in an interior surface of the enclosure and is sized and shaped to receive and engage a light assembly for illuminating an interior area of the enclosure. A lid can be pivotally attached to the sidewall and moveable between a closed position, in which the lid covers the interior of the enclosure and an open position, in which the interior of the enclosure is open and exposed. The lid can have an opening formed therethrough and a translucent or transparent insert section positioned within the opening, so that light emitted by the light assembly is visible through the insert section when the lid is in the closed position.

According to another embodiment of the invention, the insert section can have a logo formed thereon, such that the logo is illuminated by light emitted from the light assembly.

Another embodiment of the invention comprises a method of illuminating a container interior that includes providing a container comprising an interior surface having at least one recess formed therein, and a light assembly comprising at least one light member adapted to be received and retained within the recess. The light member is inserted into the recess and illuminates the interior area of the container. The light assembly can be removed from the container by pulling the light member out of the recess.

A container apparatus according to another embodiment of the invention comprises an enclosure defining an interior area and a light assembly adapted for illuminating the interior area. A substantially concave recess is formed in the interior surface of the enclosure and is adapted for receiving and maintaining the light assembly therein.

According to another embodiment of the invention, the enclosure comprises a body section and a lid section connected to the body section.

According to another embodiment of the invention, the substantially concave recess is formed in the lid section.

According to another embodiment of the invention, the substantially concave recess is formed in the body section.

According to another embodiment of the invention, the light assembly comprises at least one light emitting device selected from the group consisting of a light emitting diode, an incandescent light bulb, and an illuminated fiber optic cable.

According to another embodiment of the invention, the enclosure is comprised of a body section and a lid section. The body section comprises a substantially rectangular base and a substantially rectangular sidewall extending upwardly from the base, and the lid section is pivotally connected to the sidewall of the body section. The substantially concave recess can be formed in the interior surface of the lid section.

According to another embodiment of the invention, the enclosure comprises a body section comprising a substantially rectangular base and a substantially rectangular sidewall having a top edge, and the substantially concave recess is formed in the top edge of the sidewall.

According to another embodiment of the invention, the light assembly comprises a substantially rectangular frame adapted for positioning in the recess formed in the top edge of the sidewall, and at least one light emitting device positioned within the frame.

According to another embodiment of the invention, the enclosure comprises a base for positioning substantially horizontally on a floor surface and a sidewall extending substantially vertically from the base. The substantially concave recess comprises a first channel formed in an interior surface of the sidewall and a complementary second channel formed in the interior surface of the sidewall at a position opposed to the first channel, the first channel and the second channel extending substantially vertically from proximate a top of the sidewall to proximate a bottom of the sidewall.

According to another embodiment of the invention, the light assembly comprises a substantially flat member received in the first channel and the second channel and adapted for sliding movement therein, such that the light assembly can provide a barrier dividing the interior area defined by the enclosure into a first interior area and a second interior area.

According to another embodiment of the invention, the base is substantially rectangular and the sidewall is substantially rectangular. The sidewall comprises first and second opposed sides and third and fourth opposed sides. The first channel is formed in the first side and the second channel is formed in the second side.

A container apparatus according to another embodiment of the invention comprises a body section comprising a base and at least one sidewall extending upwardly from the base, a light emitting device adapted for illuminating at least a portion of the container apparatus, and a lid section pivotally attached to the sidewall. The lid is moveable between a closed position in which the lid covers an interior area of the body and an open position in which the interior area of the body is exposed. The lid has an opening formed therethrough and an insert section positioned within the opening. The insert section is translucent or transparent, such that light emitted by the light assembly is visible through the insert section when the lid is in the closed position.

A container apparatus according to another embodiment of the invention comprises an enclosure defining an interior area, and at least one substantially concave recess formed in the interior surface of the enclosure. The recess is adapted for receiving and maintaining an insert assembly therein.

According to another embodiment of the invention, the apparatus includes an insert assembly. The insert assembly can be comprised of a light emitting device adapted for illuminating the interior area of the enclosure, an audio speaker adapted for emitting sound, and/or a dry box container adapted for storing items.

According to another embodiment of the invention, the insert assembly can be comprised of at least one temperature altering element. The temperature altering element can be a cooling element adapted for cooling the interior area of the enclosure and/or a heating element adapted for heating the interior area of the enclosure.

According to another embodiment of the invention, the enclosure comprises a body comprising a substantially rectangular base and a substantially rectangular sidewall extending upwardly from the base defining four corners of the body, and wherein the at least one recess comprises four recesses formed at said four corners.

According to another embodiment of the invention, the enclosure further comprises a lid pivotally connected to the body.

According to another embodiment of the invention, the apparatus includes an insert assembly comprising four elongate insert members positioned within the four recesses. Each of the four elongate insert members comprises at least one temperature altering element, such as a cooling element or a heating.

According to another embodiment of the invention, the insert assembly includes a substantially rectangular insert member positioned above the four elongate insert members and supported by a top edge of the sidewall. The substantially rectangular insert member includes at least one light emitting device adapted for illuminating the interior area of the enclosure.

According to another embodiment of the invention, a container apparatus includes means for deactivating corona viruses, including the Coronavirus disease 2019 (COVID-19) caused by the severe acute respiratory syndrome coronavirus 2 (SARS-CoV-2).

According to another embodiment of the invention, one or more recesses can be formed in a vehicle, such as a boat or ship. The recesses can be formed in the ship's hull. Each recess can be sized and shaped to receive and engage a complementary insert member. Each insert member can be comprised of a battery powered light emitting device for illuminating the water around the ship. The light emitting devices can project light of various colors. Wireless technology, such as the wireless communication technology sold under the mark "BLUETOOTH", can be used to operatively connect the light emitting devices to a remote control that can turn the light emitting devices on and off.

Another embodiment of the invention comprises a method of altering or manipulating the wavelength of light.

Another embodiment of the invention comprises a light apparatus in which the effective wavelength of the light emitted by the apparatus can be altered and/or manipulated using a lens and/or a computing device.

An embodiment of the invention comprises a light apparatus comprising an ultraviolet light emitting device and a translucent lens adapted to lower the wavelength of the light emitted from the light apparatus. According to an embodiment of the invention, the ultraviolet light emitting device emits light at a wavelength of 250-320 nanometers (nm) and the lens lowers the wavelength of the light to 220-249 nanometers.

According to an embodiment of the invention, the lens is glazed, frosted, tinted and/or etched, whereby upon contacting the lens the wavelength of the light emitted from the ultraviolet light is lowered.

According to an embodiment of the invention, the light apparatus includes a housing containing the ultraviolet light emitting device therein, and the translucent lens forms part of the housing. The light apparatus can deliver ultraviolet light having a wavelength in an optimum wavelength range of 220-249 nm for deactivating viruses, bacteria, molds and other pathogens using 250-290 wavelength ultraviolet lights.

Another embodiment of the invention comprises a light apparatus comprising a light emitting device and a motherboard comprising a micro-controller operatively connected to the light emitting device, wherein the motherboard can control the wattage delivered to the light emitting device.

Another embodiment of the invention comprises a sanitizing light apparatus adapted for use in a refrigerator or freezer comprising at least one ultraviolet light.

Another embodiment of the invention comprises a sanitizing apparatus adapted for use in an auxiliary power outlet comprising at least one ultraviolet light. According to an embodiment of the invention, the light apparatus can be operatively connected to an automobile auxiliary power outlet and used to clean air within the automobile.

Another embodiment of the invention comprises an apparatus for sanitizing the air within a structure. The apparatus comprises a magnetic member and at least one ultraviolet light. According to an embodiment of the invention, the apparatus can be attached to an air vent and used to clean air circulating through the vents.

Another embodiment of the invention comprises a method of disinfecting one or more items. The method can include providing a container apparatus comprising an enclosure, the enclosure defining an interior area and comprising a base, a sidewall extending upwardly from the base, and a lid pivotally connected to the sidewall. The lid is moveable between an open position in which the interior area is exposed and a closed position in which the interior area is covered by the lid. A light emitting device is positioned within the interior area of the enclosure. The light emitting device emits ultraviolet light having a wavelength in the range of 100 to 280 nanometers. One or more items to be disinfected can be positioned within the enclosure, and the lid is moved to the closed position. Ultraviolet light is emitted from the light emitting device for one to ten minutes.

Another embodiment of the invention comprises a method for deactivating viruses, bacteria, and other pathogens.

Another embodiment of the invention comprises a method for deactivating corona viruses, including the Coronavirus disease 2019 (COVID-19) caused by the severe acute respiratory syndrome coronavirus 2 (SARS-CoV-2).

DETAILED DESCRIPTION OF PREFERRED EMBODIMENTS

Figure 1:
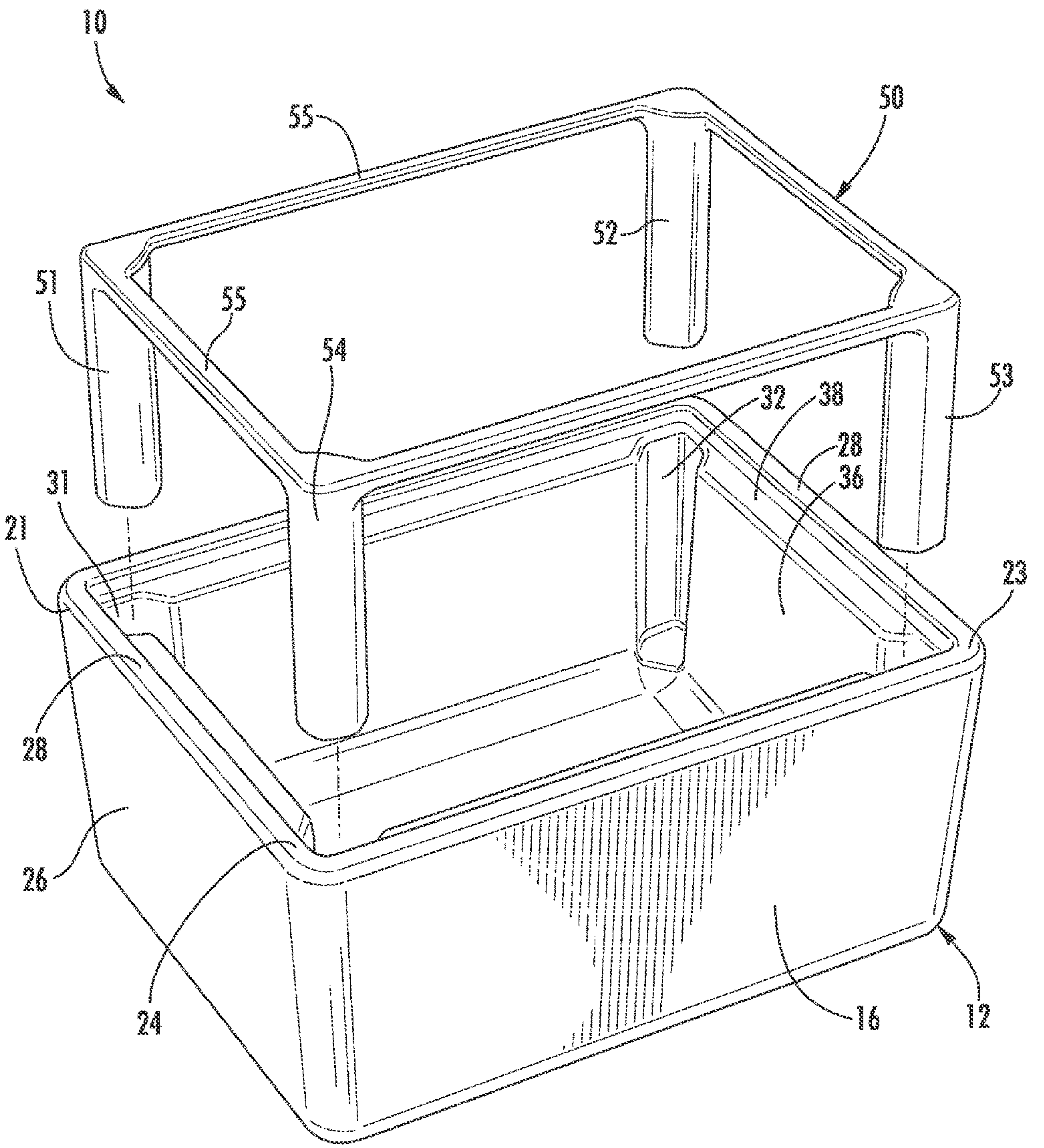
FIG. 1 is a perspective view of a container apparatus of according to a preferred embodiment of the invention.
Figure 2:
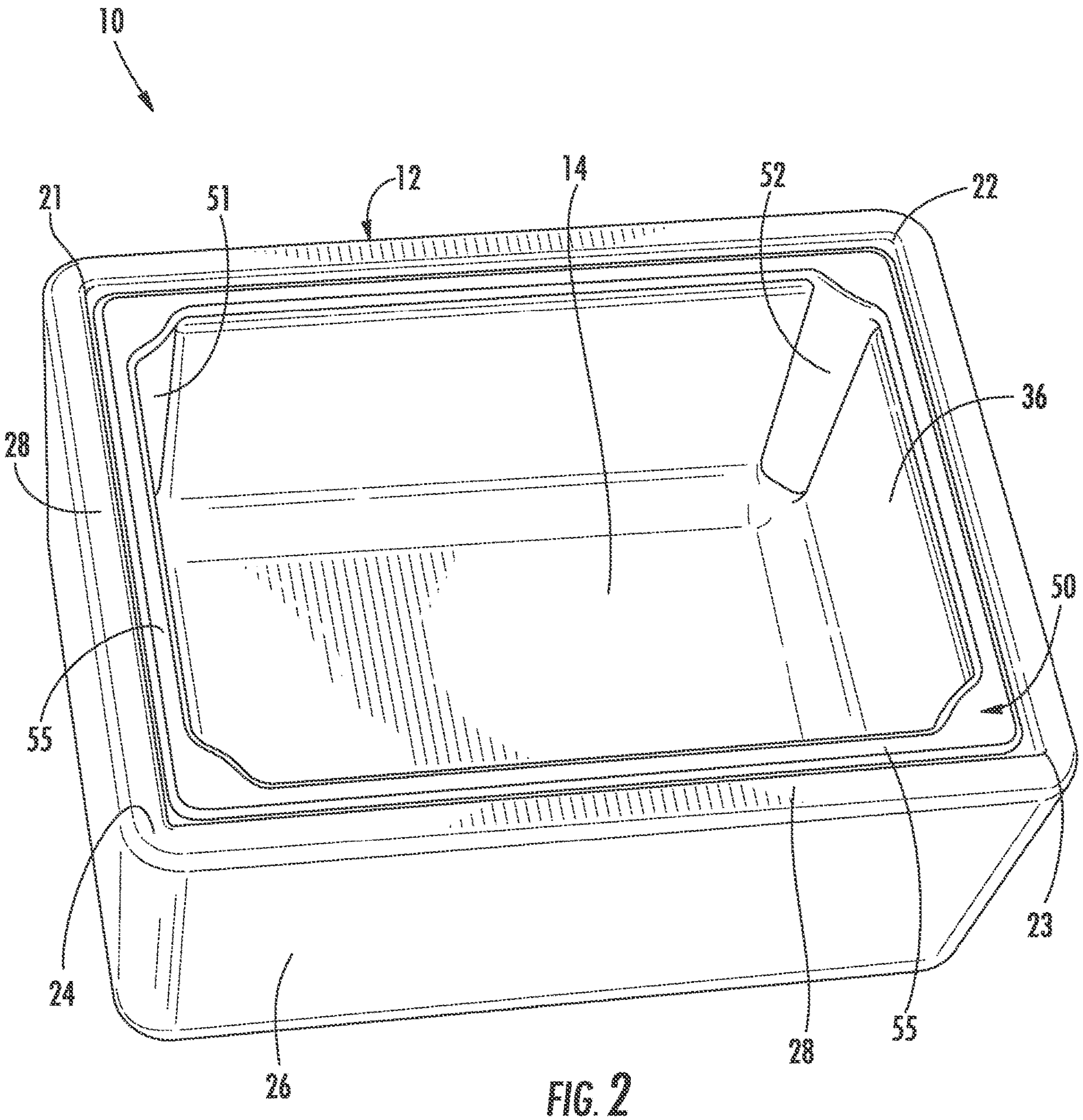
FIG. 2 is another perspective view of the container apparatus of FIG. 1.
Figure 3:
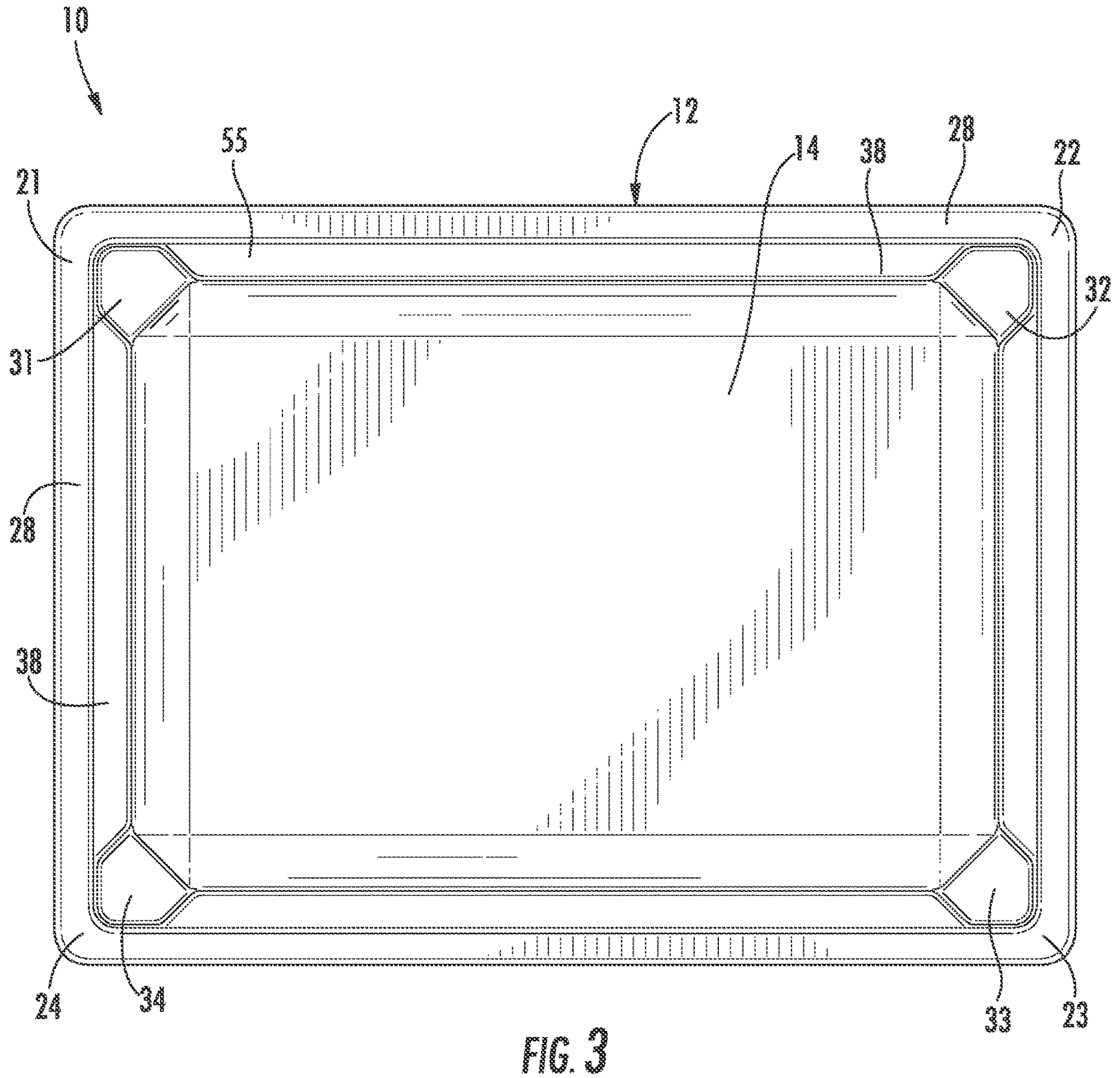
FIG. 3 is a top plan view of the container apparatus of FIG. 1, without a light assembly.

A container apparatus according to a preferred embodiment of the invention is illustrated in FIGS. 1-3, and shown generally at reference numeral 10. As shown in FIG. 1, the apparatus 10 comprises a container 12 and a light assembly insert 50. The word "container" as used herein refers generally to any kind of enclosure. For example, the apparatus 10 can comprise a thermally insulated cooler adapted for storing food and beverages. Alternatively, the container 10 can comprise a toolbox for storing tools, or other type of enclosure. The terms "disinfect", "disinfecting", "sanitize", "sanitizing", and "germicidal" as used herein refer generally to an apparatus or process that reduces, destroys, deactivates, and/or eliminates pathogenic agents, such as viruses, bacteria and fungi.

As shown in FIGS. 1-3, the container 12 comprises a substantially rectangular base 14, and a substantially rectangular sidewall 16 extending upwardly from the base 14. The sidewall 16 has four sides defining four corners 21, 22, 23, 24. The sidewall 16 is comprised of an outer wall section 26 and an inner wall section 36, as shown in FIGS. 1 and 2. The surface of the inner wall section 36 defines an interior surface of the container 12. The top 38 of the inner wall section 36 is lower than the top 28 of the outer wall section 26, thereby creating a tiered rest platform 38, as shown in FIG. 1. The container 12 can be made of plastic or other suitable material, and can be made by injection molding or other suitable manufacturing process. It is to be noted that while container apparatus 10 comprises a substantially rectangular container 12, the invention is not so limited. Alternatively, the container 12 can be a variety of shapes, such as substantially circular, oval and square.

Four substantially concave and elongate recesses 31, 32, 33, 34 are formed in the inner wall section 36 proximate the four corners 21, 22, 23, 24, respectively, of the sidewall 16, as shown in FIG. 1. The recesses 31, 32, 33, 34 begin at the top 38 of the inner wall section 36 and extend downwardly to the base 14 of the container 12, as shown at reference numeral 32 in FIG. 1. The recesses 31, 32, 33, 34 can have a substantially pentagonal shape, as shown in FIG. 3.

The light assembly 50 comprises four elongate light members 51, 52, 53, 54 attached to a rectangular top frame 55, as shown in FIG. 1. Each of the four light members 51 are attached at one of the four corners of the rectangular frame 55, and extend downwardly from the rectangular frame member at an angle of about ninety degrees, as shown in FIG. 1.

The elongate recesses 31, 32, 33, 34 in the container 12 are sized and shaped to conform to the elongate light members 51, 52, 53, 54, in order to receive and retain the light members 51, 52, 53, 54 therein. Accordingly, light members 51, 52, 53, 54 have a length approximately equal to the length of the recesses 31, 32, 33, 34 extending from the top 38 of the inner wall section 36 to the base 14, and have a perimeter slightly less than the effective perimeter of the recesses 31, 32, 33, 34, such that the light members 51, 52, 53, 54 can be inserted into the recesses 31, 32, 33, 34, as shown in FIGS. 1 and 2, and retained within the recesses 31, 32, 33, 34 by frictional engagement.

The rectangular frame 55 of the light assembly 50 has a perimeter approximately equal to the perimeter of the rectangular rest platform 38. As such, the frame 55 rests on the rest platform 38 of the inner wall section 36 when the light members 51, 52, 53, 54 are fully inserted into the recesses 31, 32, 33, 34, as shown in FIG. 2. The frame 55 has a height approximately equal to the difference in height between the top edge 28 of the outer wall section 26 and the top edge 38 of the inner wall section 36, such that the top of the frame 55 sits flush with the top 28 of the outer wall section 26 when the light members 51, 52, 53, 54 are fully inserted into the recesses 31, 32, 33, 34, as shown in FIG. 2.

Alternative embodiments can utilize an additional engagement mechanism for facilitating retention of the light members 51, 52, 53, 54 within the recesses 31, 32, 33, 34. For example, a plurality of protuberances can be positioned on the outer surface of the light members 51, 52, 53, 54 to engage a plurality of corresponding openings formed on the portion of the inner wall section 36 defining the recesses 31, 32, 33, 34 when the light members 51, 52, 53, 54 are fully inserted into the recesses 31, 32, 33, 34. The protuberances residing within the openings further retain the light members 51, 52, 53, 54 within the recesses 31, 32, 33, 34. Alternatively, a plurality of protuberances can be formed on the portion of the inner wall section 36 defining the recesses 31, 32, 33, 34 to engage a plurality of corresponding apertures formed in the light members 51, 52, 53, 54 when the light members 51, 52, 53, 54 are inserted into the recesses 31, 32, 33, 34.

Each elongate light member 51, 52, 53, 54 is comprised of a light emitting device, such as a light emitting diode (LED), a low-voltage incandescent light bulb, illuminated fiber optic cables, or other suitable light emitting device. As such, whenever it is desired to emit light into the interior of the container 12, the light assembly 50 is positioned within the container 12 by inserting the light members 51, 52, 53, 54 into the recesses 31, 32, 33, 34, as shown in FIGS. 1 and 2, and turning on the light emitting devices of the light members 51, 52, 53, 54. In an alternative embodiment, each light member 51, 52, 53, 54 can include a battery powered cooling or heating element. In another alternative embodiment, each elongate member 51, 52, 53, 54 comprises a battery powered cooling or heating element, with no light emitting device.

According to a preferred embodiment of the invention, each elongate light member 51, 52, 53, 54 comprises a germicidal light emitting device. Preferably, each light member 51, 52, 53, 54 comprises a light emitting device that emits ultraviolet light having a wavelength of 100 nanometers to 280 nanometers (UV-C). The light members 51, 52, 53, 54 are preferably LED UV-C lights. The light members 51, 52, 53, 54 emit UV-C light that can inactivate various microbes, such as viruses, including Coronavirus disease 2019 (COVID-19), bacteria, molds and other pathogens. The light members 51, 52, 53, 54 emit UV-C light that deactivates the DNA of viruses, bacteria and other pathogens, thereby destroying their ability to multiply and cause disease. In addition, the UV-C light emitted by the light members 51, 52, 53, 54 helps to keep food in the container 12 fresh by destroying bacteria, and helps prevent foul odors from developing in the container 12 by destroying odor causing microbes.

According to a preferred embodiment, each light member 51, 52, 53, 54 comprises an LED emitting UV-C light having a wavelength of 265 nm. According to another preferred embodiment, each light member 51, 52, 53, 54 comprises an excimer lamp emitting UV-C light at a wavelength of 222 nm. According to another preferred embodiment, each light member 51, 52, 53, 54 comprises a mercury vapor lamp with a peak emission at 254 nm.

Preferably, the light emitting device is powered by disposable or rechargeable batteries. The light emitting devices can be set on a timer such that they automatically turn off after a certain period of time to avoid draining of the batteries. In a preferred embodiment, the light emitting devices turn off after ten minutes of light emission. The light assembly 50 is not wired to or otherwise electrically connected to the container 12, and no electric wiring is located within the container 12. As such, the light assembly 50 can be easily removed from the container 12 to repair a malfunction in one of the light members 51, 52, 53, 54, or replace drained batteries. Also, the light assembly 50 can be removed when there is no desire for illumination within the container 12 or when it is desired to replace the light assembly 50 with a new unit. Since the light assembly 50 is not operatively connected to or functionally dependent upon the container 12, and can be easily removed from the container 12, the light assembly 50 and container 12 can be manufactured, distributed and/or sold as separate units. Alternatively, the light assembly 50 and container 12 can be distributed and/or sold as components of a container kit.

In an alternative embodiment, the apparatus 10 can include a lid 70, shown in FIGS. 12-16. The lid 70 can be pivotally attached to top of the sidewall 16 of the container 10 via two hinge members 71, 72, shown in FIGS. 14 and 16.

An embodiment of the invention comprises a method of disinfecting items using the container apparatus 10. Items to be disinfected are placed within the interior of the container 12. The items can be food, beverages, packages and/or other items. The light assembly 50 is turned on, and the lid 70 is closed. UV-C light is emitted from the light members 51, 52, 53, 54 and deactivates viruses, bacteria, and other pathogens present on the items. The lid 70 can be opened, and the items can be removed from the container 12. In another embodiment, the container apparatus 10 can be used to transport human tissue, such as blood and/or organs. Another embodiment of the invention comprises a method of decontaminating liquid. A liquid, such as water, is placed within the container 12, and the UV-C light members 51, 52, 53, 54 are activated to destroy harmful microbes present in the water.

Another embodiment of the invention comprises a method of deactivating COVID-19 present on items such, as food, beverages, packages and/or other items. Items to be disinfected can be placed within the interior of the container apparatus 10. The lid 70 is closed, and the light assembly 50 is turned on. Preferably, each light member 51, 52, 53, 54 emits UV-C light at a wavelength of 200-265 nm for one to ten minutes. Most preferably, each light member 51, 52, 53, 54 emits UV-C light at a wavelength of 254-265 nm for eight minutes. The UV-C light deactivates viruses, including COVID-19, present on the items. It is believed that the UV-C light breaks the chemical bonds that hold the molecular structure of COVID-19, and a Log 2 reduction (99.0%-99.9%) of COVID-19 can be attained. The lid 70 can then be opened, and the items can be removed from the container apparatus 10.

According to a preferred embodiment of the invention, some of the light members emit germicidal ultraviolet light, while other light members comprise light emitting devices that emit light that is visible to the human eye. For example, light members 51, 53 can be comprised of UV-C LED lights, and light members 52, 54 can be LED lights that emit light having a wavelength of about 380-740 nanometers. As such, light members 51, 53 deactivate viruses, bacteria and other microbes within the container 12, while light members 52, 54 light up the interior of the container 12 and assist the user in seeing items inside the container.

The lid 70 can be operatively connected to the light assembly 50, so that the light assembly 50 comes on when the lid 70 is closed. In an alternative embodiment, the lid 70 can be operatively connected to the light assembly 50, such that the light assembly 50 comes on when the lid is opened.

Figure 12:
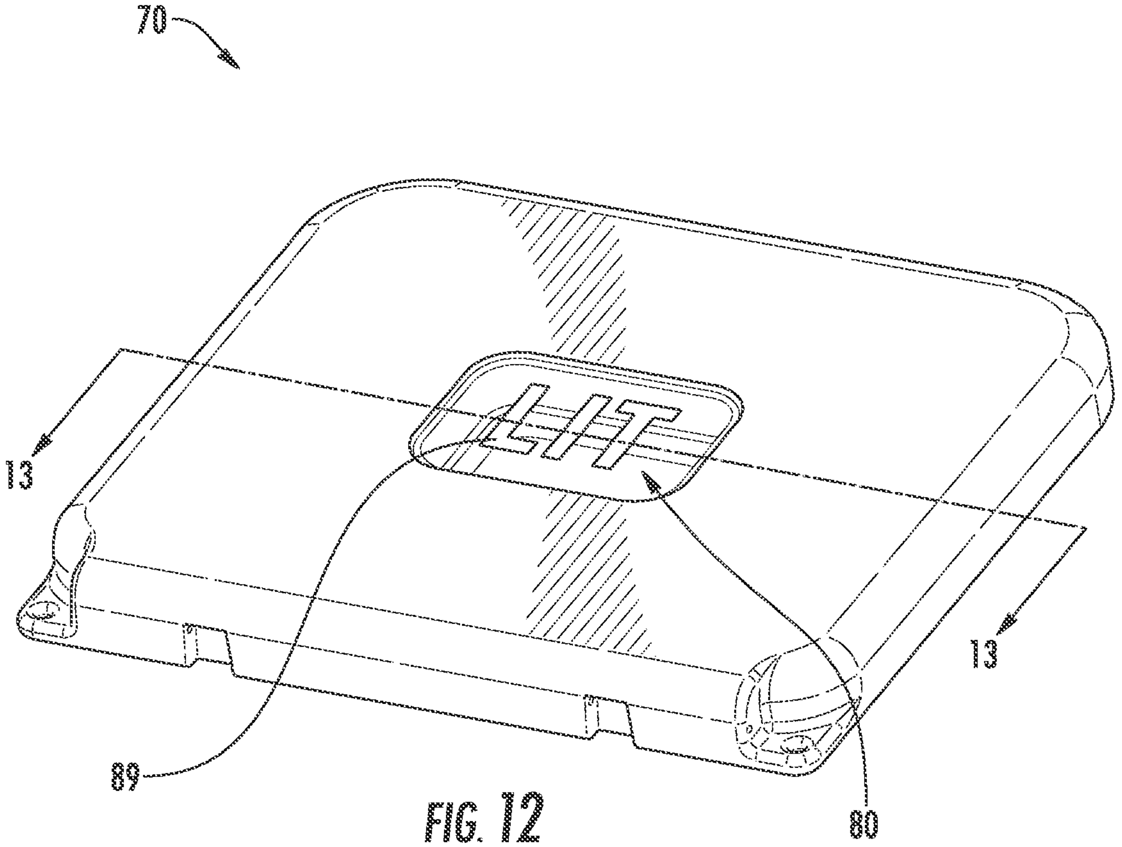
FIG. 12 is a perspective view of a lid portion of a container apparatus according to a preferred embodiment of the invention.
Figure 13:
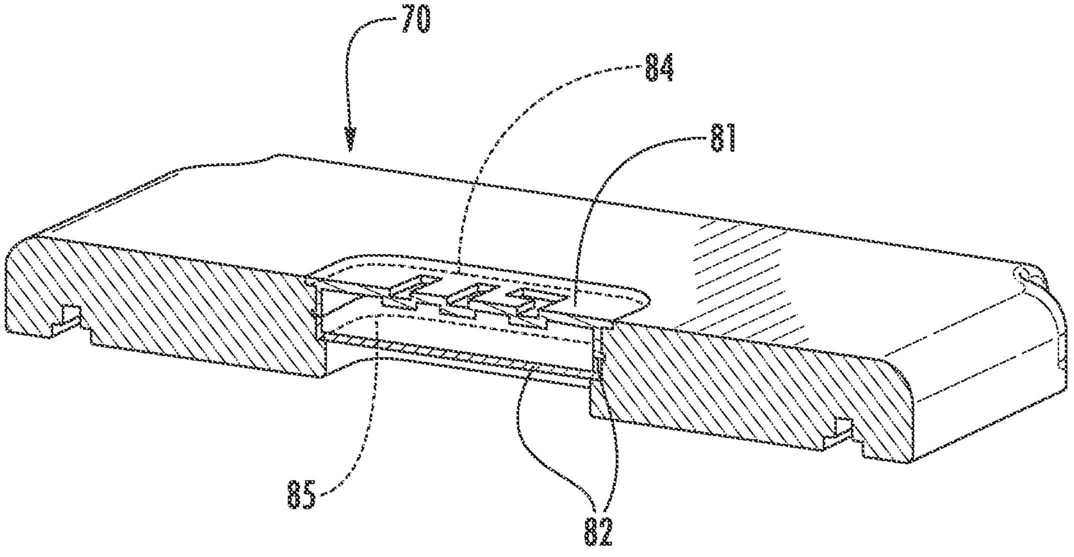
FIG. 13 is a cross sectional perspective view of the lid of FIG. 12, taken along lines 13-13 in FIG. 12.
Figure 14:
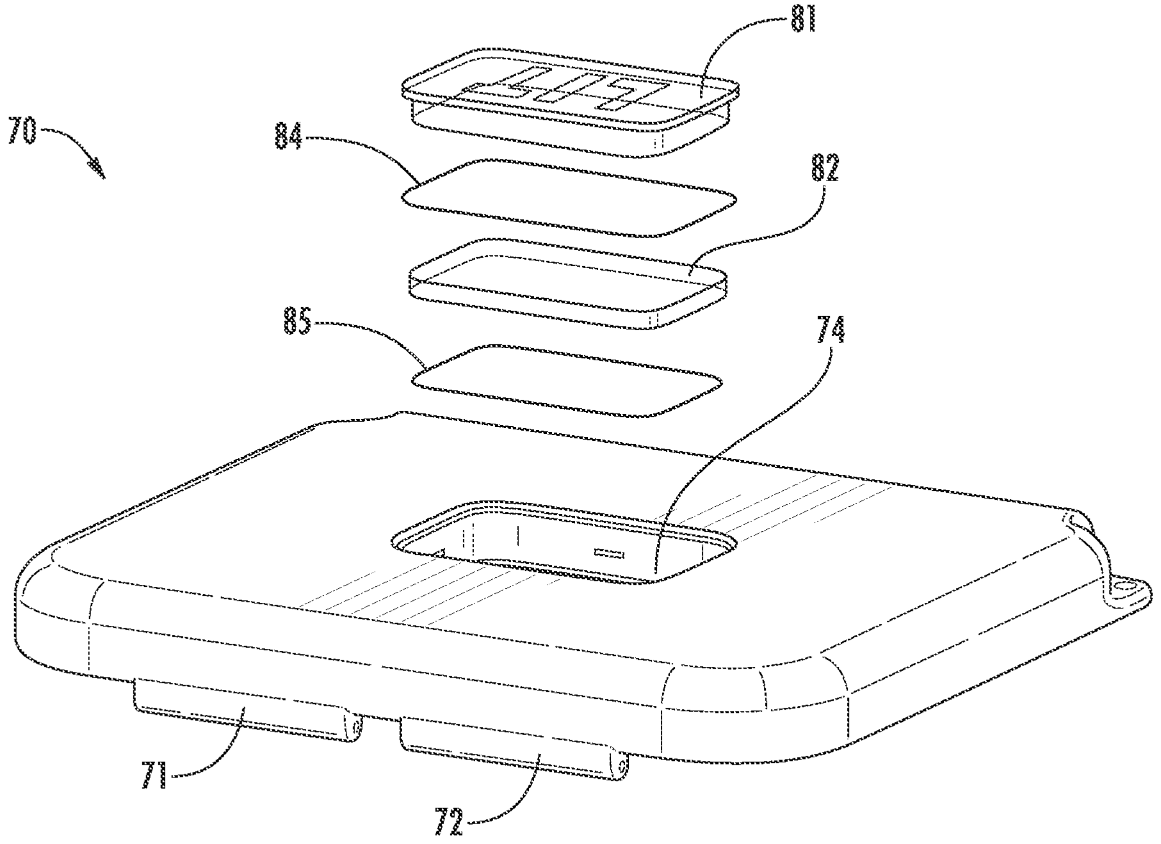
FIG. 14 is an exploded perspective view of the lid of FIG. 12.
Figure 15:
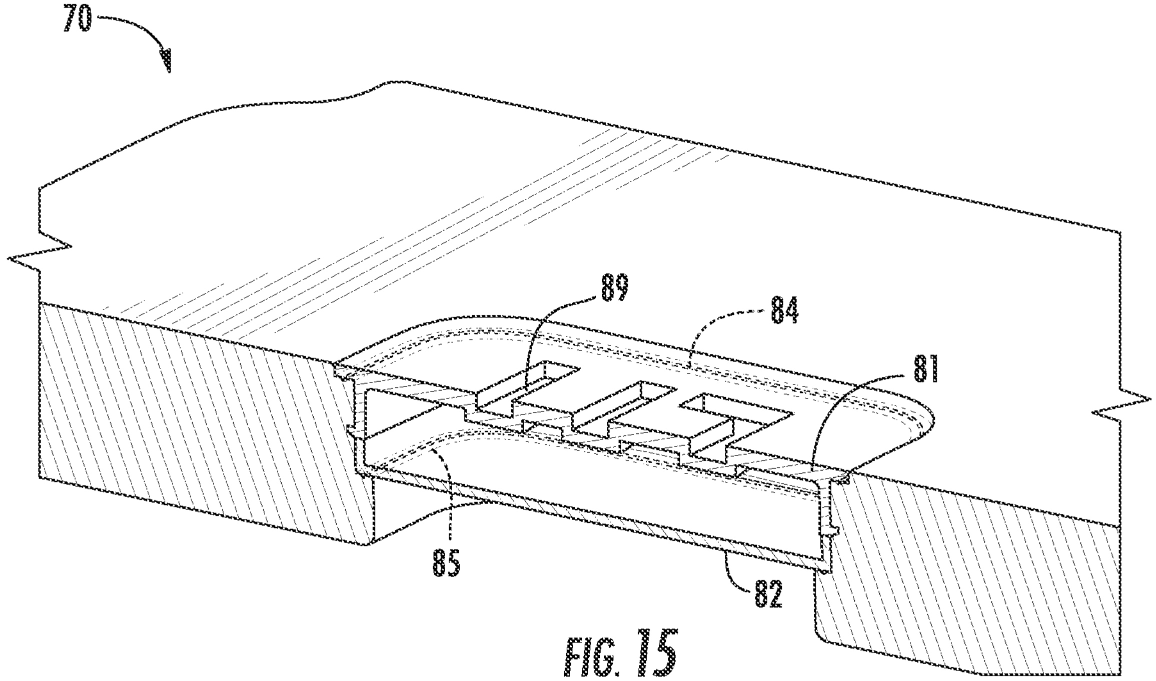
FIG. 15 is an enlarged partial perspective view of the lid of FIG. 12.
Figure 16:
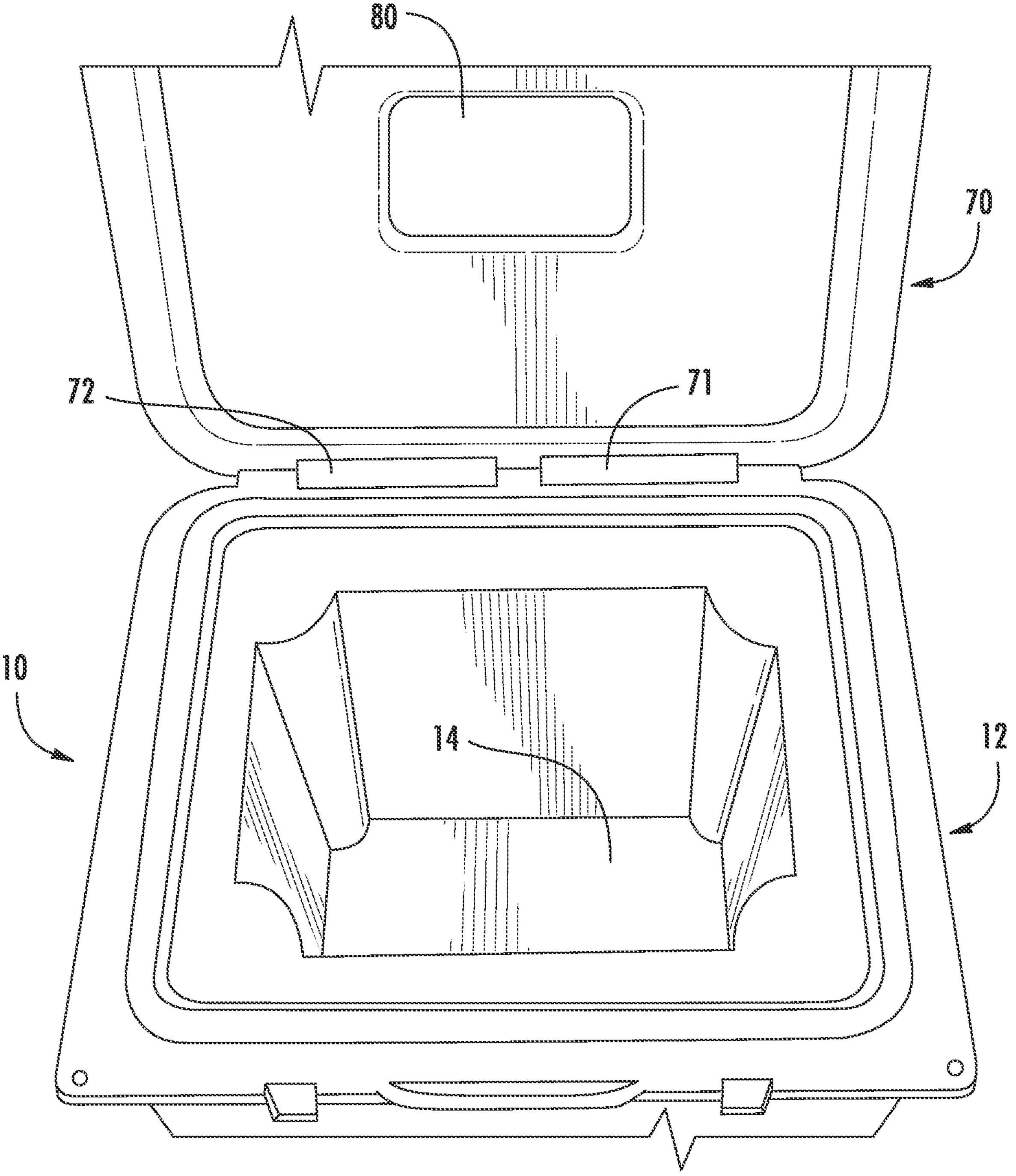
FIG. 16 is a perspective view of a container apparatus with a lid according to a preferred embodiment of the invention.

The lid 70 can include a center insert 80 positioned within a central opening 74 formed in the center of the lid 70, as shown in FIGS. 12-14. The center insert 80 and the central opening 74 can be substantially rectangular, as shown in FIGS. 12 and 14. The center insert 80 is comprised of an upper insert section 81 and a lower insert section 82, and two sealing rings 84, 85. The insert sections 81, 82 are made of a transparent or translucent material, such as polycarbonate plastic. The sealing rings 84, 85 are made of a sealing material, such as injection molded silicone. One sealing ring 84 is positioned along a recessed top edge of the central opening 74, below the top surface of the upper insert section 81, as shown in FIGS. 13 and 15. The other sealing ring 85 is positioned below the lower insert section 82 on a recessed ledge formed within the central opening 74, as shown in FIG. 13. Because the insert sections 81, 82 are translucent or transparent, light emitting from the light assembly 50 is visible through the insert section 80. A logo 89, shown as “LIT” in FIG. 12, can be engraved on the top surface of the upper insert section 81. The logo 89 can comprise any alphanumeric characters and/or graphics, such as a company name, trademark, sports team and/or school name or insignia. Light emitting from the light assembly 50 can shine through the insert 80 when the lid 70 is closed on the container 10, thereby illuminating the logo 89 and making it more visible. Alternatively, the insert section 80 can also include a light emitting device, such as a light emitting diode. It should be noted that while the lid 70 is described above as being a part of container 10, the lid 70 can also be used with other embodiments of the invention, including the container 100 described below.

Alternatively, the center insert 80 can be comprised of an audio speaker unit, such as a wireless audio speaker having wireless communications technology sold under the mark “BLUETOOTH”. In another alternative embodiment, the center insert 80 can be a dry box container for holding personal items, such as keys, wallets and the like. The container can be made of rubber, plastic or other suitable material.

Figure 4:
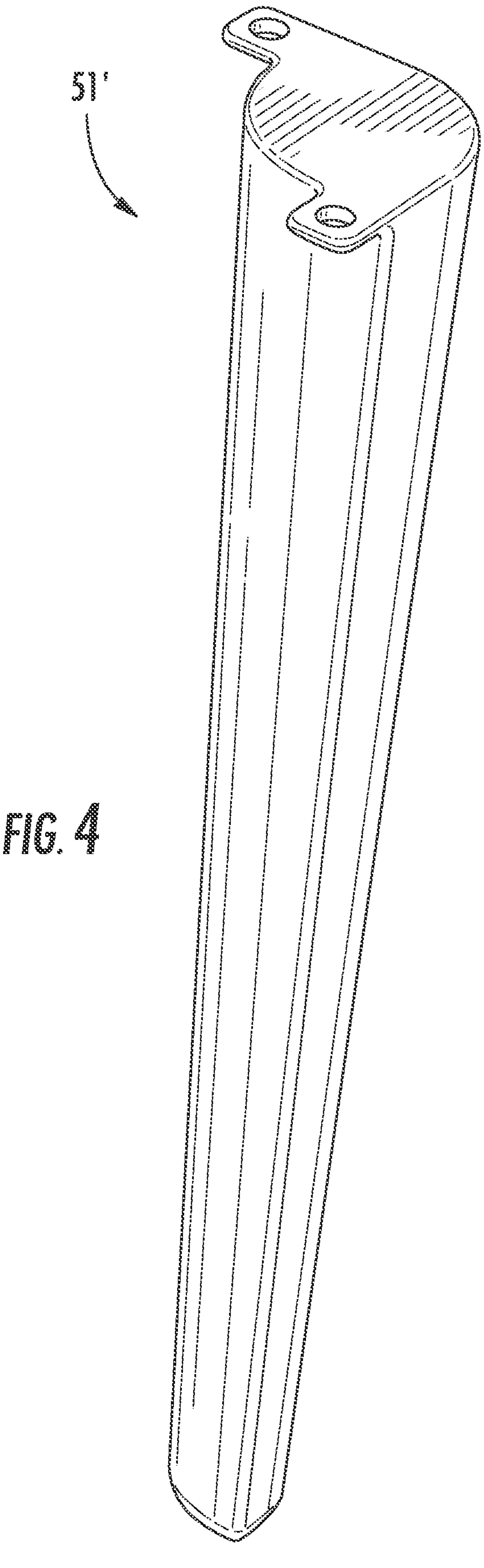
FIG. 4 is a perspective view of a light assembly according to another preferred embodiment of the invention.
Figure 5:
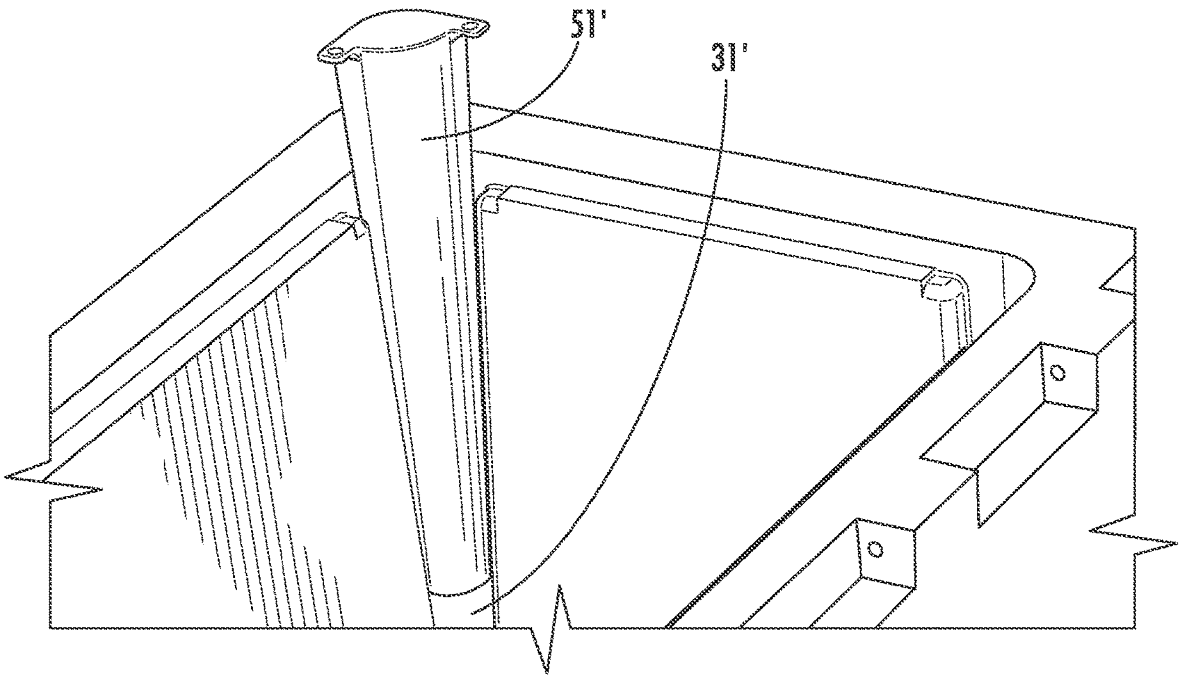
FIG. 5 is a partial perspective view of a container apparatus according to another preferred embodiment of the invention.
Figure 6:
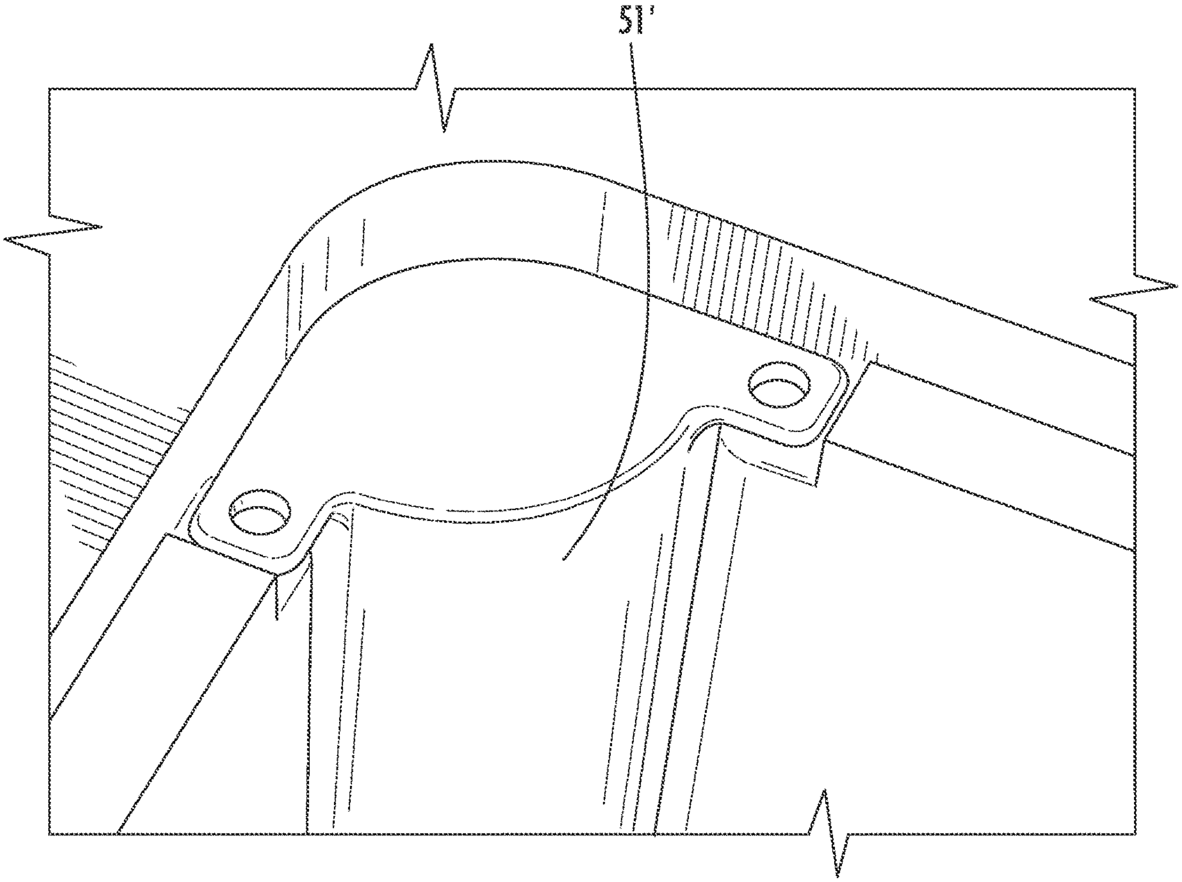
FIG. 6 is another partial perspective view of the container apparatus of FIG. 5.

In another preferred embodiment of the invention, shown in FIGS. 4-6, the light assembly comprises a plurality of separate elongate light members 51'. As such, the light assembly does not include a rectangular frame joining the light members 51' together, as in the previously described light assembly 50. In this alternative embodiment, each light member 51' is separately positioned into a recess 31', as shown in FIGS. 5 and 6.

Figure 7:
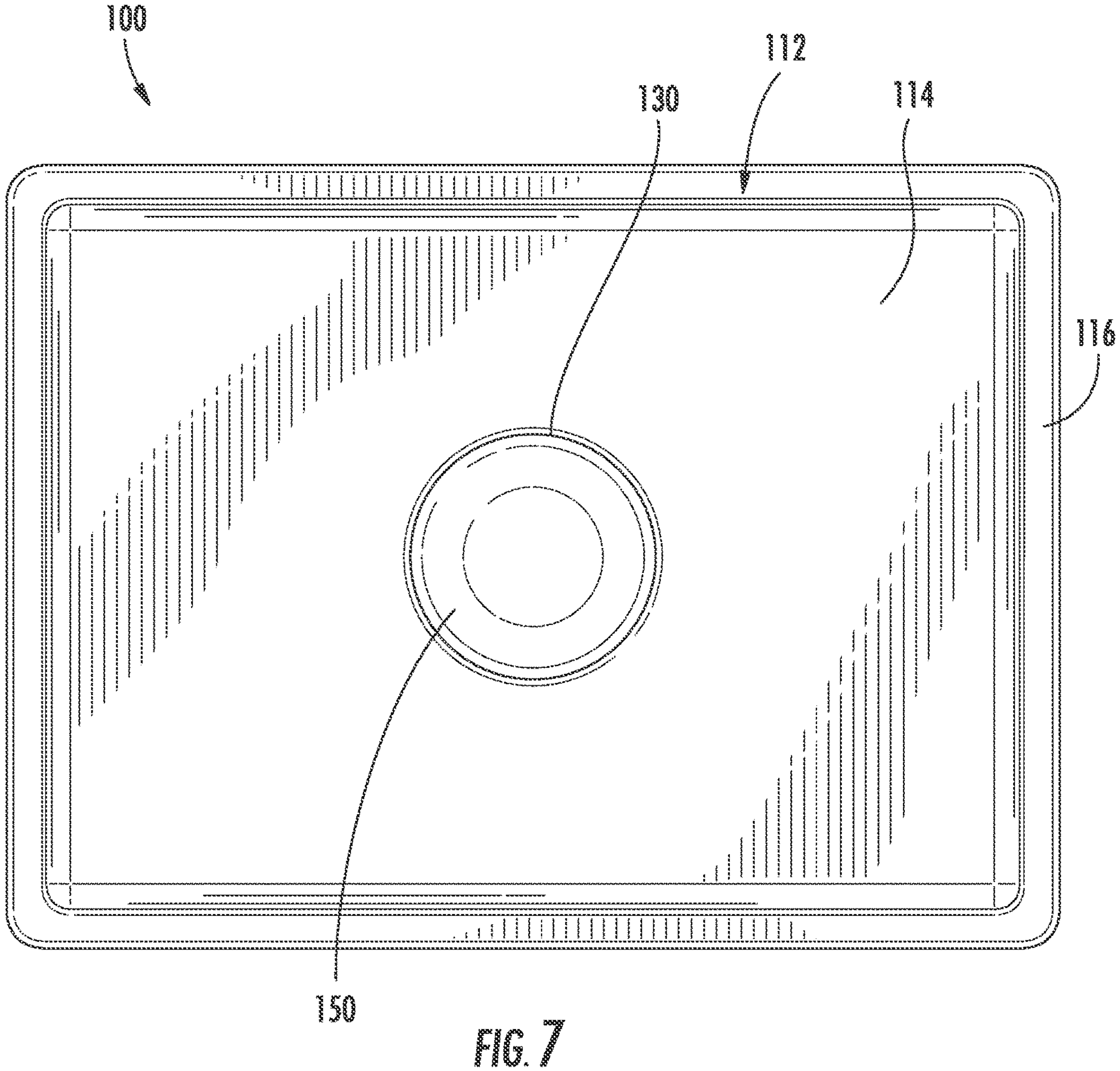
FIG. 7 is a top plan view of a container apparatus according to another preferred embodiment of the invention.

A container apparatus according to another preferred embodiment of the invention is illustrated in FIGS. 7-11 and shown generally at reference numeral 100. As shown in FIG. 7, the apparatus 100 comprises a container 112 and a light assembly 150.

Figure 8:
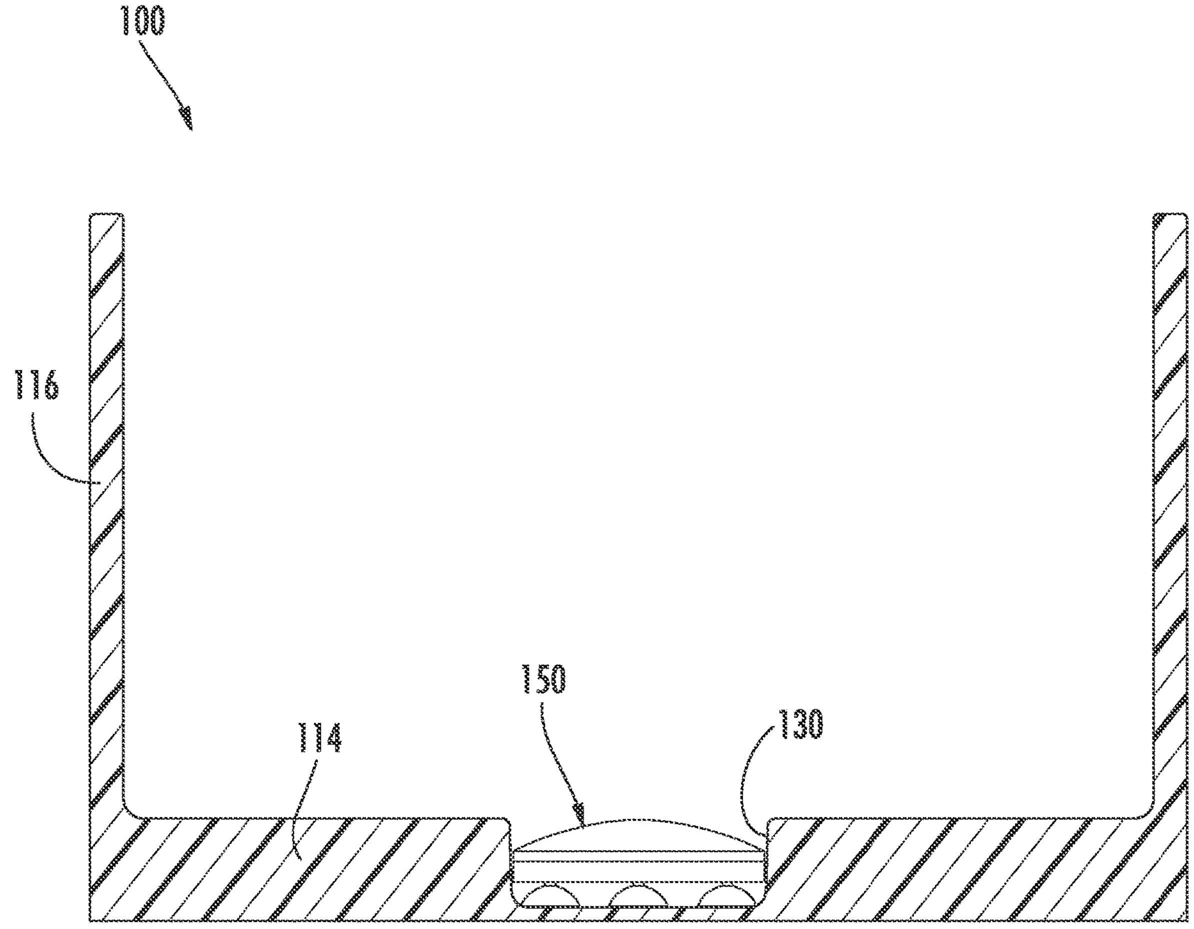
FIG. 8 is a side cross sectional view of the container apparatus of FIG. 7; mom

As shown in FIG. 7, the container 112 comprises a substantially rectangular base 114, and a substantially rectangular sidewall 116 extending upwardly from the base 14. A concave recess 130 is formed proximate the center of the base, as shown in FIG. 8. The recess 130 can have a circular shape, as shown in FIG. 7.

Figure 9:
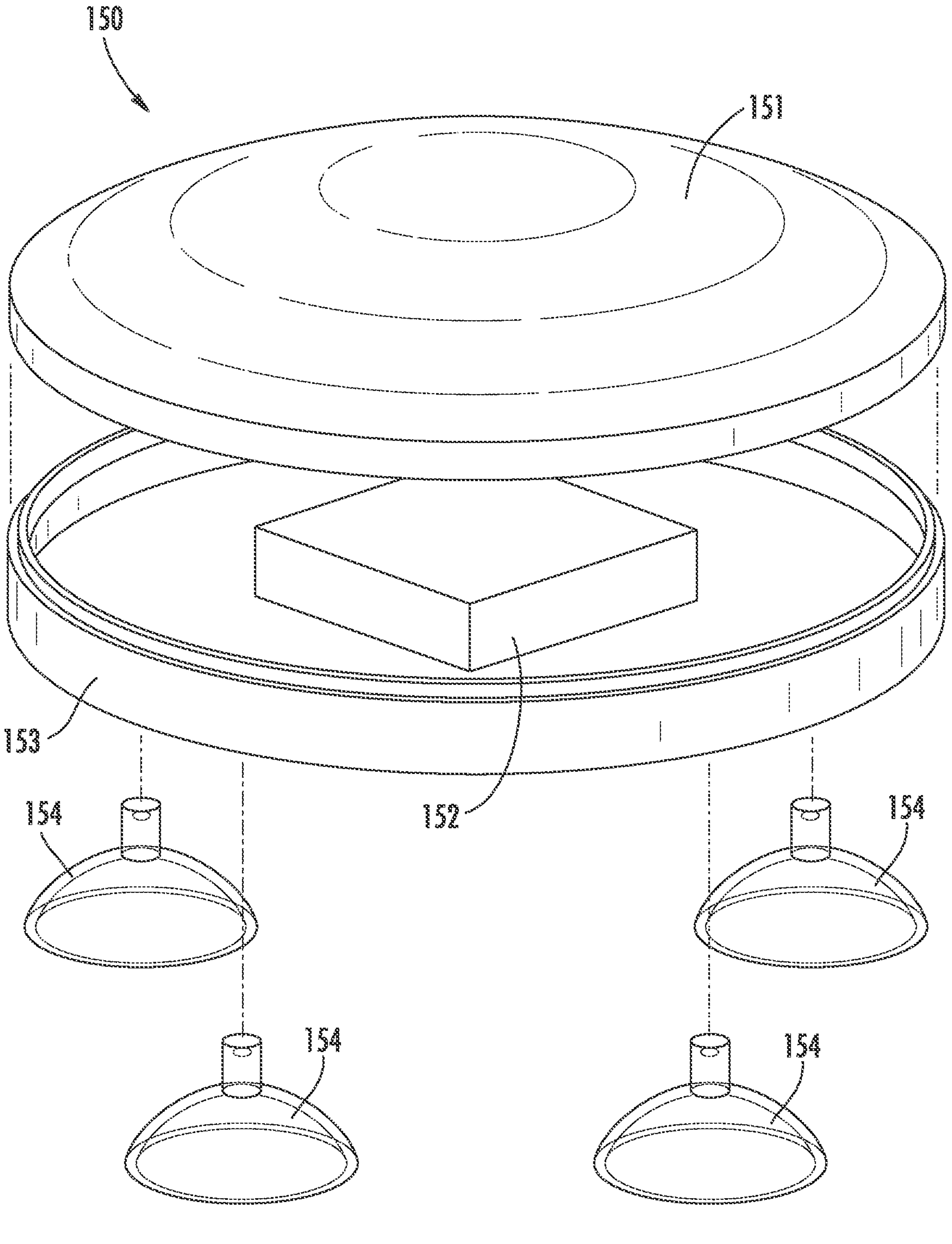
FIG. 9 is an exploded cross sectional view of a light assembly according to another preferred embodiment of the invention.
Figure 10:
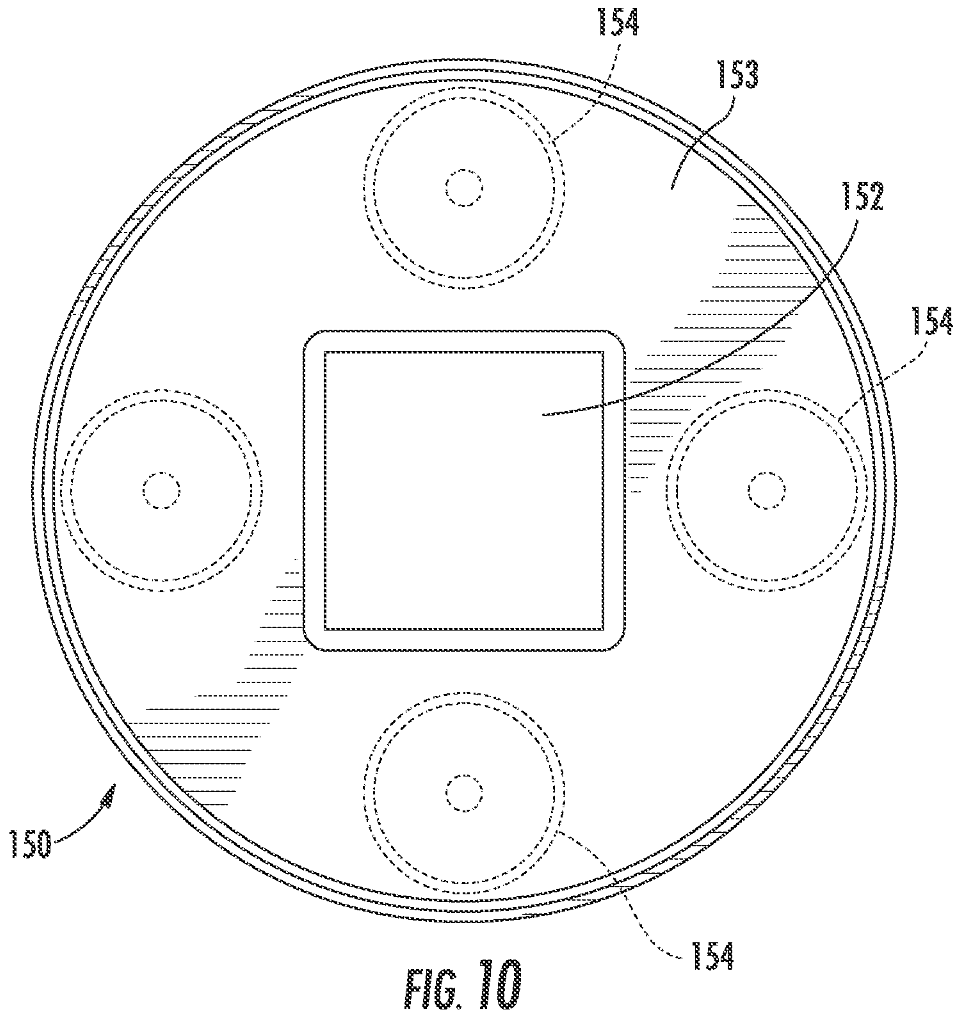
FIG. 10 is a top plan view of the light assembly of FIG. 9.
Figure 11:
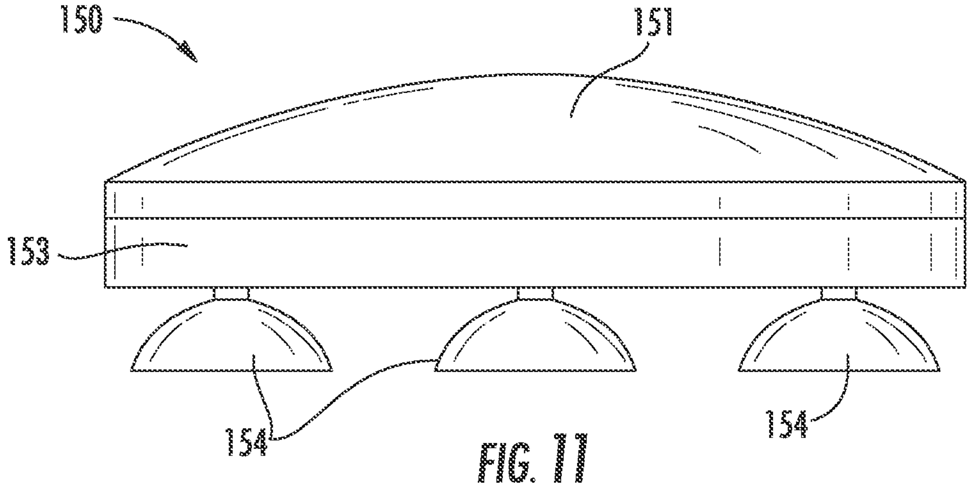
FIG. 11 is a side elevation of the light assembly of FIG. 9.

As shown in FIGS. 9-11, the light assembly 150 comprises a disc shaped light emitting member 151 containing a battery compartment 152, and a plurality of suction cups 154 attached to the base section 153 of the light emitting member 151. The light emitting member 151 can be comprised of any light emitting device, such as a light emitting diode (LED), an incandescent light bulb, or illuminated fiber optic cables.

As shown in FIG. 8, the light assembly 150 can be positioned within the circular recess 130 formed in the center of the base 114. Firmly pressing down on the light assembly 150 causes suction cups 154 to engage the base 114 and prevent the light assembly from coming out of the recess 130 during transport of the container 112.

Figure 17:
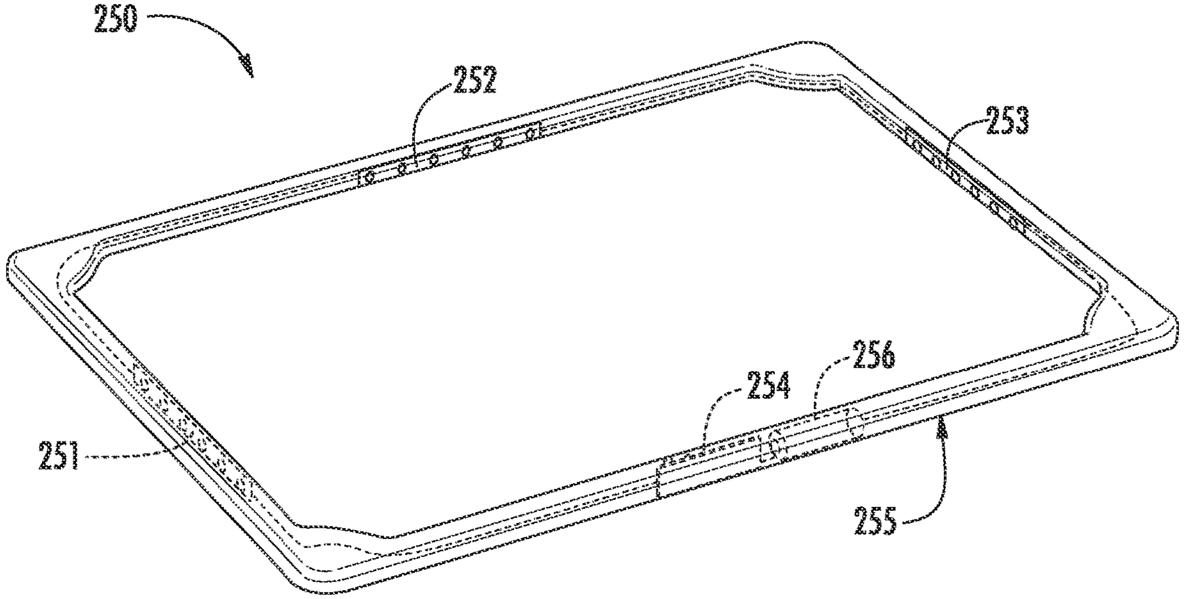
FIG. 17 is a perspective view of a light assembly insert according to another preferred embodiment of the invention.
Figure 18:
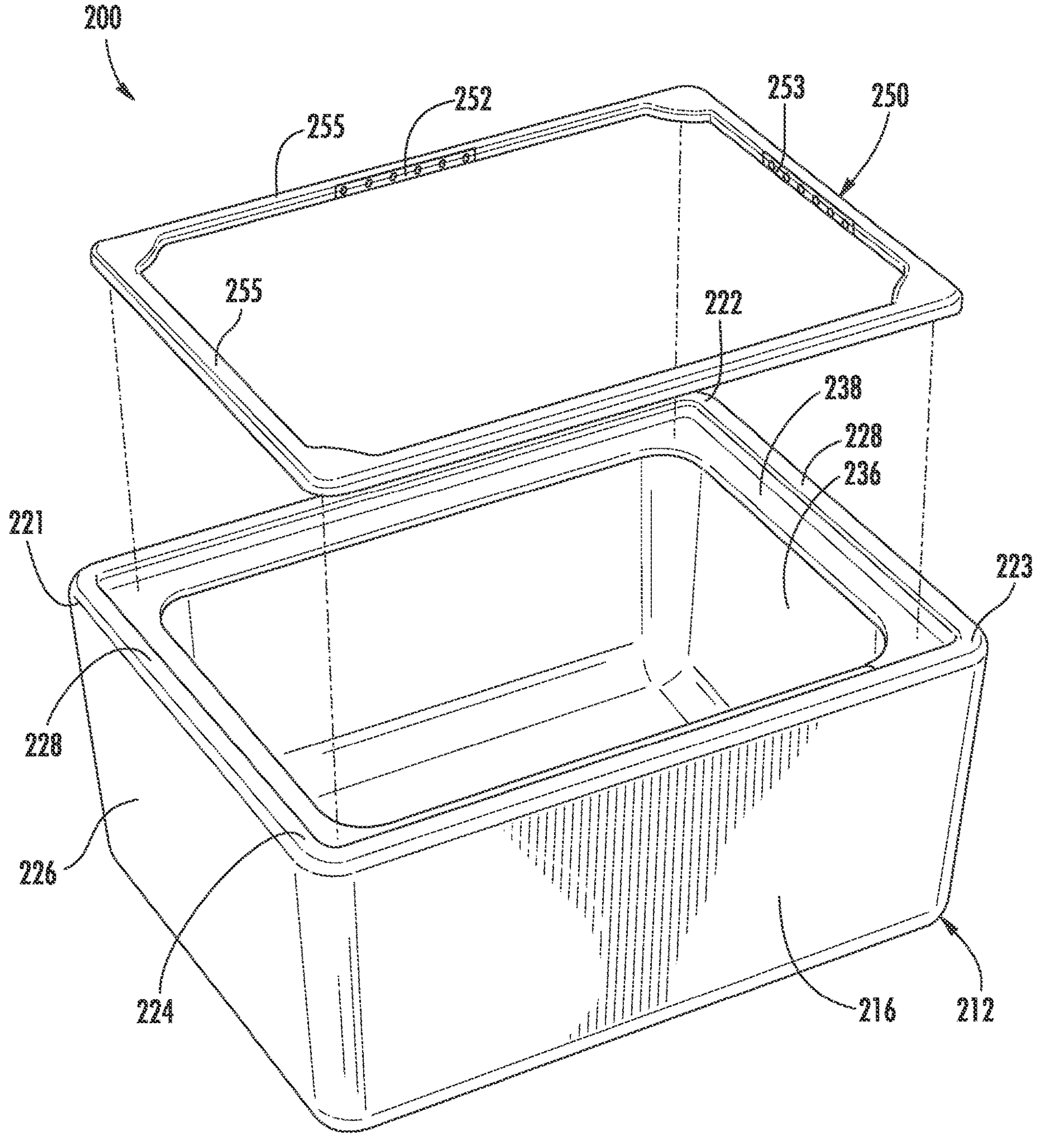
FIG. 18 is a perspective view of a container apparatus according to another preferred embodiment of the invention.
Figure 19:
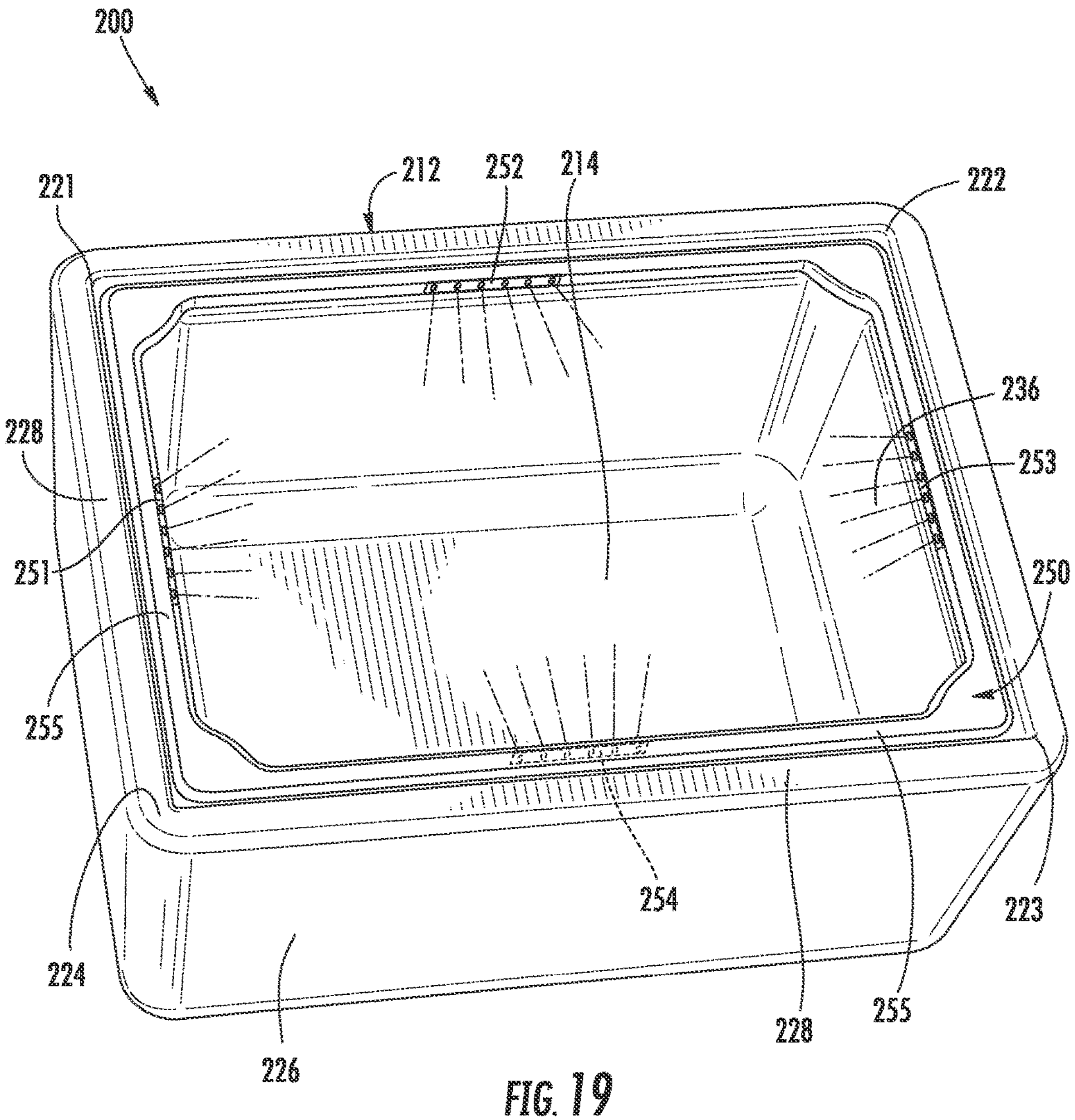
FIG. 19 is another perspective view of the container apparatus of FIG. 18.

A container apparatus according to another preferred embodiment of the invention is illustrated in FIGS. 17-19 and shown generally at reference numeral 200. As shown in FIG. 18, the apparatus 200 comprises a container 212 and a light assembly insert 250 that can be positioned within the container 212. The container 212 can be made of plastic or other suitable material and can be made by injection molding or other suitable manufacturing process.

The light assembly insert 250 comprises a substantially rectangular frame 255, and a plurality of light emitting devices 251, 252, 253, 254 positioned in the frame 255 as shown in FIG. 17. The light emitting devices 251-254 can be comprised of light emitting diodes (LED). Alternatively, the light emitting devices 251-254 can comprise low-voltage incandescent light bulbs, illuminated fiber optic cables, or other suitable light emitting devices. The light assembly 250 can include a power source for powering the light emitting devices 251-254, such as a battery 256 housed within the frame 255 and operatively connected to the light emitting devices 251-254, as shown in FIG. 17.

The light assembly insert 250 can be positioned within a substantially concave recess formed in the interior surface of the container 212. As shown in FIGS. 18-19, the container 212 comprises a substantially rectangular base 214, and a substantially rectangular sidewall 216 extending upwardly from the base 214. The sidewall 216 has four sides defining four corners 221, 222, 223, 224. The sidewall 216 is comprised of an outer wall section 226 and an inner wall section 236, as shown in FIGS. 18 and 19. The top 238 of the inner wall section 236 is lower than the top 228 of the outer wall section 226, forming a substantially concave recess in the sidewall 216 defining a tiered rest platform 238, as shown in FIG. 18.

The rectangular frame 255 of the light assembly 250 has a perimeter approximately equal to the perimeter of the substantially rectangular rest platform 238. The rest platform 238 is sized and shaped to receive the light assembly 250 and support the light assembly 250 thereon, as shown in FIGS. 18 and 19. The light assembly frame 255 has a depth (or height) approximately equal to the difference in height between the top edge 228 of the outer wall section 226 and the top edge 238 of the inner wall section 236, such that the top of the frame 255 sits substantially flush with the top 228 of the outer wall section 226 when the light assembly 250 is positioned in the rest platform 238, as shown in FIG. 19.

As such, the light assembly 250 can be easily installed and removed from the container 212 depending on the needs or desires of the user. When the user wishes to illuminate the interior of the container 212, the light assembly 250 is positioned on the rest platform 238, as shown in FIG. 19. The light assembly 250 is securely retained within the rest platform 238 during movement of the container 212. When the user does not want to illuminate the interior of the container 212, the user can lift up on the light assembly 250 and remove it from the container 212.

Figure 20:
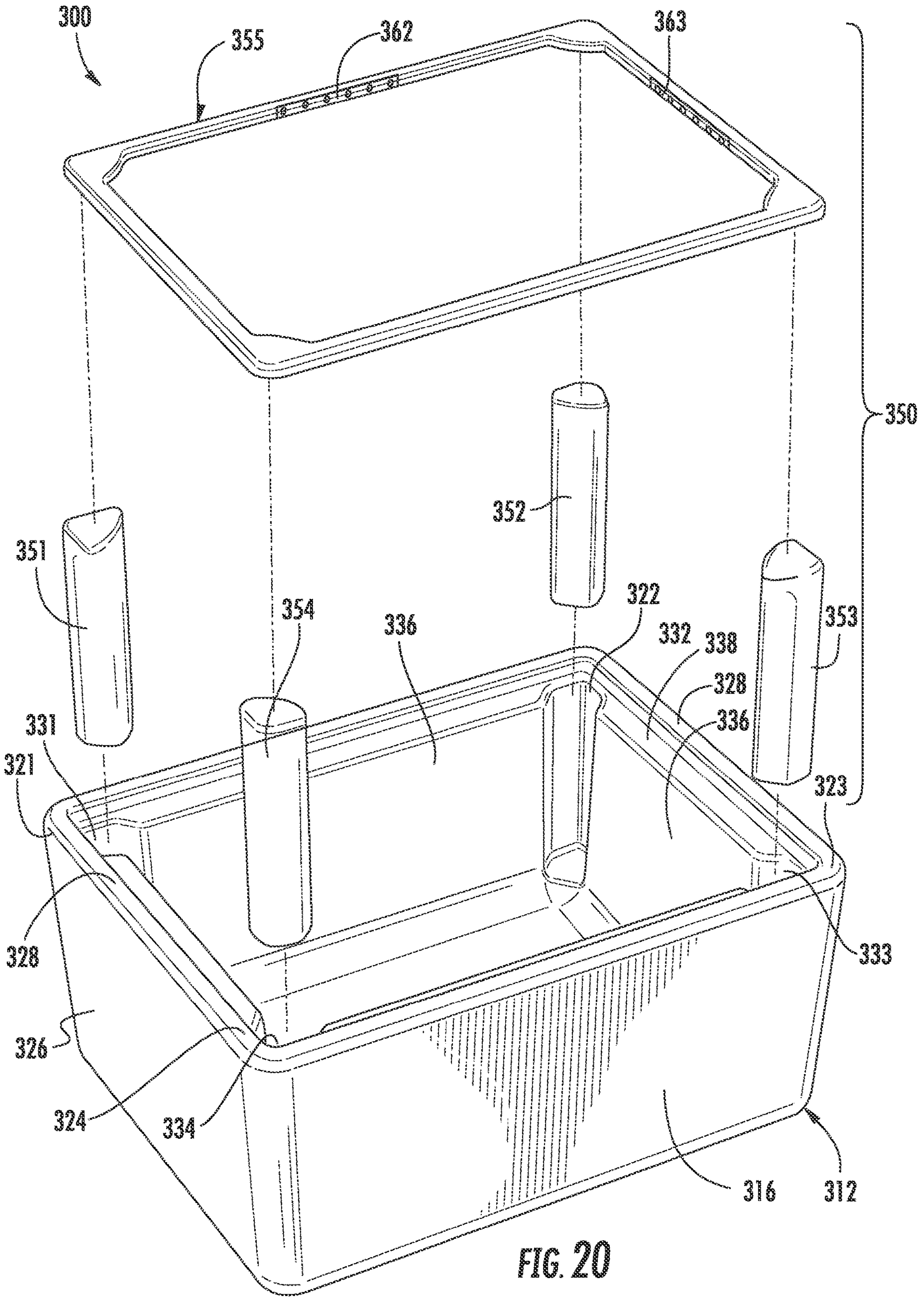
FIG. 20 is a perspective view of a container apparatus according to another preferred embodiment of the invention.
Figure 21:
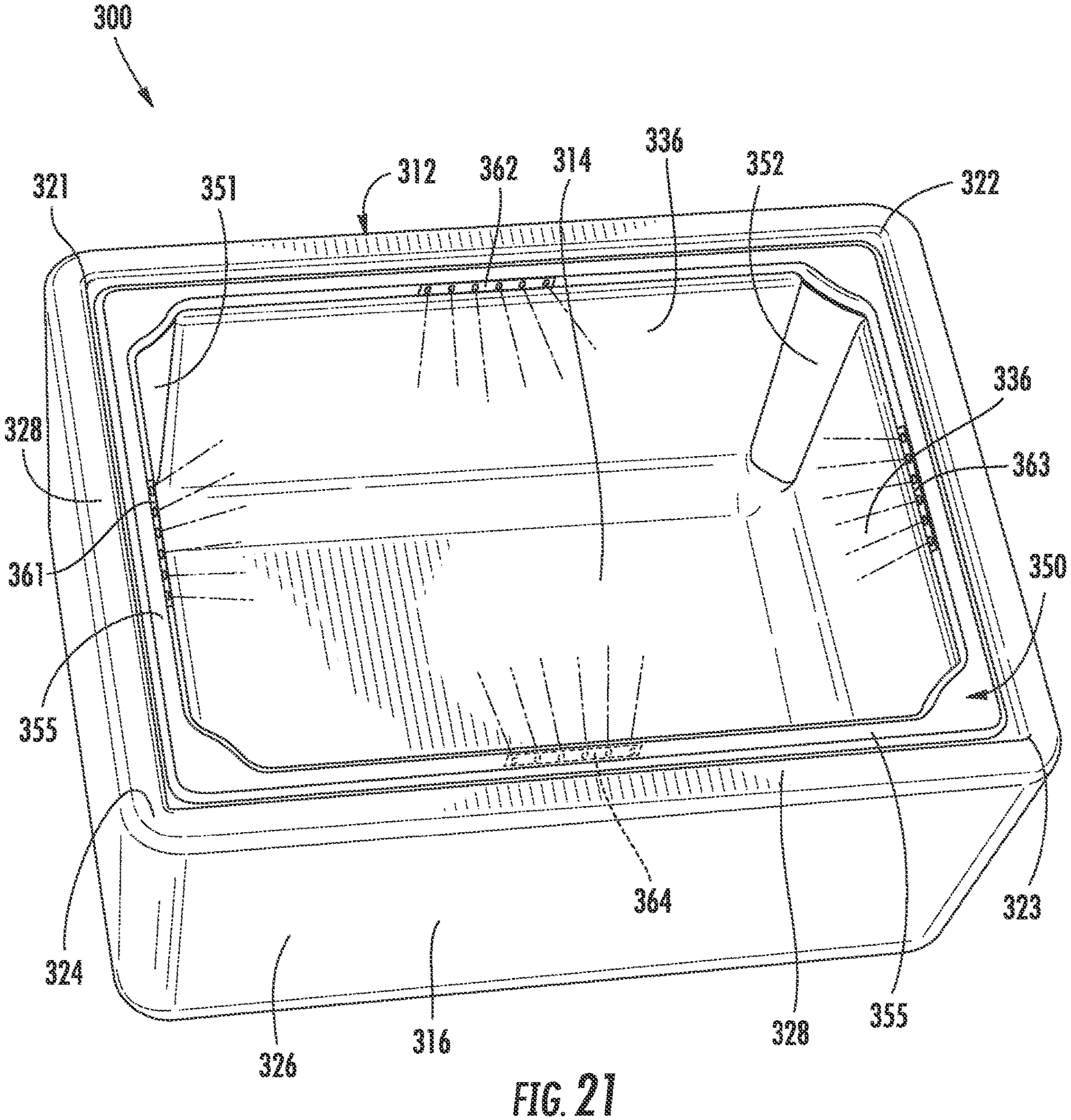
FIG. 21 is another perspective view the container apparatus of FIG. 20.

A container apparatus according to another preferred embodiment of the invention is illustrated in FIGS. 20 and 21, and shown generally at reference numeral 300. The container apparatus 300 comprises a container 312 having an interior surface that is adapted for receiving and releasably maintaining an insert assembly 350 therein. The container 312 can be made of plastic or other suitable material, and can be made by injection molding or other suitable manufacturing process.

As shown in FIGS. 20 and 21, the container 312 comprises a substantially rectangular base 314, and a substantially rectangular sidewall 316 extending upwardly from the base 314. The sidewall 316 has four sides defining four corners 321, 322, 323, 324. The sidewall 316 is comprised of an outer wall section 326 and an inner wall section 336, as shown in FIGS. 20 and 21. The surface of the base 314 and the surface of the inner wall section 336 define interior surfaces of the container 312. The top 238 of the inner wall section 236 is lower than the top 328 of the outer wall section 326, thereby creating a tiered rest platform 338, as shown in FIG. 20.

Four substantially concave and elongate recesses 331, 332, 333, 334 are formed in the inner wall section 336 proximate the four corners 321, 322, 323, 324, respectively, of the sidewall 316, as shown in FIG. 20. The recesses 331, 332, 333, 334 begin at the top 338 of the inner wall section 336 and extend downwardly to the base 314 of the container 312, as shown at reference numeral 332 in FIG. 20. The recesses 331, 332, 333, 334 can have a substantially pentagonal shape.

The insert assembly 350 can comprise four elongate insert members 351, 352, 353, 354, shown in FIG. 20. The elongate insert members 351, 352, 353, 354 can be temperature altering elements adapted to alter the temperature within the container 12. Each temperature altering member 351, 352, 353, 354 can be comprised of a vessel containing a refrigerant gel, such as a gel formulation comprised of propylene glycol and water or other suitable materials. Other refrigerant gel compositions are disclosed in U.S. Pat. No. 4,357,809, which is incorporated herein.

The elongate recesses 331, 332, 333, 334 in the container 312 are sized and shaped to conform to the elongate members 351, 352, 353, 354, in order to receive and retain the elongate members 351, 352, 353, 354 therein. Accordingly, elongate members 351, 352, 353, 354 have a length approximately equal to the length of the recesses 331, 332, 333, 334 extending from the top 338 of the inner wall section 336 to the base 314, and have a perimeter slightly less than the effective perimeter of the recesses 331, 332, 333, 334, such that the elongate members 351, 352, 353, 354 can be inserted into the recesses 331, 332, 333, 334, as shown in FIGS. 20 and 21, and retained within the recesses 331, 332, 333, 334 by frictional engagement.

Prior to being positioned into the container 312, the temperature altering members 351, 352, 353, 354 can be stored in a freezer or refrigerator. When the container 312 is to be used to keep items cool, the elongate members 351, 352, 353, 354 are removed from the freezer/refrigerator and positioned into the elongate recesses 331, 332, 333, 334 of the container 312, as described above. As such, the cooled elongate members 351, 352, 353, 354 cool the interior surface and interior area of the container 312, thereby helping to maintain the stored items at a cooler temperature for a longer period of time. Alternatively, the temperature altering members 351, 352, 353, 354 can comprise a heating gel, such as gels that can be heated in the microwave typically used in heating packs. Each member 351, 352, 353, 354 comprises a vessel made of material such as plastic that is safe for placement in a microwave. As such, the heated elongate members 351, 352, 353, 354 can heat the interior area of the container 312 to maintain the stored items at a warmer temperature for a longer period of time. In yet another alternative embodiment, the elongate members 351, 352, 353, 354 comprise a gel material that can be used for both heating and cooling. As such, the user can selectively use the elongate members 351, 352, 353, 354 for cooling by storing them in a freezer or refrigerator prior to use, or use the members 351, 352, 353, 354 for heating by heating the members 351, 352, 353, 354 in a microwave before use.

The insert assembly 350 comprises a substantially rectangular top frame 355 having a plurality of light emitting devices 361, 362, 363, 364 positioned in the frame 355 as shown in FIGS. 20 and 21. The light emitting devices 361, 362, 363, 364 can emit light at a wavelength visible to humans, such as 380-740 nanometers. The light emitting devices 361-364 can be comprised of light emitting diodes (LED). Alternatively, the light emitting devices 361-364 can comprise low-voltage incandescent light bulbs, illuminated fiber optic cables, or other suitable light emitting devices. The frame 355 can include a power source for powering the light emitting devices 361-364, such as a battery housed within the frame 355 and operatively connected to the light emitting devices 361-364, as shown in FIG. 17.

As shown in FIGS. 20 and 21, the top 338 of the inner wall section 336 is lower than the top 328 of the outer wall section 326, forming a substantially concave recess in the sidewall 316 defining a tiered rest platform 338, as shown in FIG. 20. The rectangular frame 355 of the light assembly 350 has a perimeter approximately equal to the perimeter of the substantially rectangular rest platform 338. The rest platform 338 is sized and shaped to receive the frame 350 and support the frame 350 thereon, as shown in FIGS. 20 and 21. The frame 355 has a depth (or height) approximately equal to the difference in height between the top edge 328 of the outer wall section 326 and the top edge 338 of the inner wall section 336, such that the top of the frame 355 sits substantially flush with the top 328 of the outer wall section 326 when the frame 355 is positioned in the rest platform 338, as shown in FIG. 21. As such, the interior of the container 312 can be illuminated by the light emitting devices 361-364 of the top frame 355, and the interior of the container 312 can be cooled or heated by the temperature altering members 351, 352, 353, 354.

According to a preferred embodiment of the invention, some of the insert members 351, 352, 353, 354 comprise temperature altering elements, and the other insert members comprise germicidal ultraviolet lights. For example, insert members 351, 353 can comprise temperature altering elements, while each of the other insert members 352, 354 can be comprised of a UV-C LED light. As such, insert members 351, 353 can alter the temperature of the interior of the container 12, and insert members 352, 354 can deactivate viruses, bacteria and other pathogens.

Figure 22:
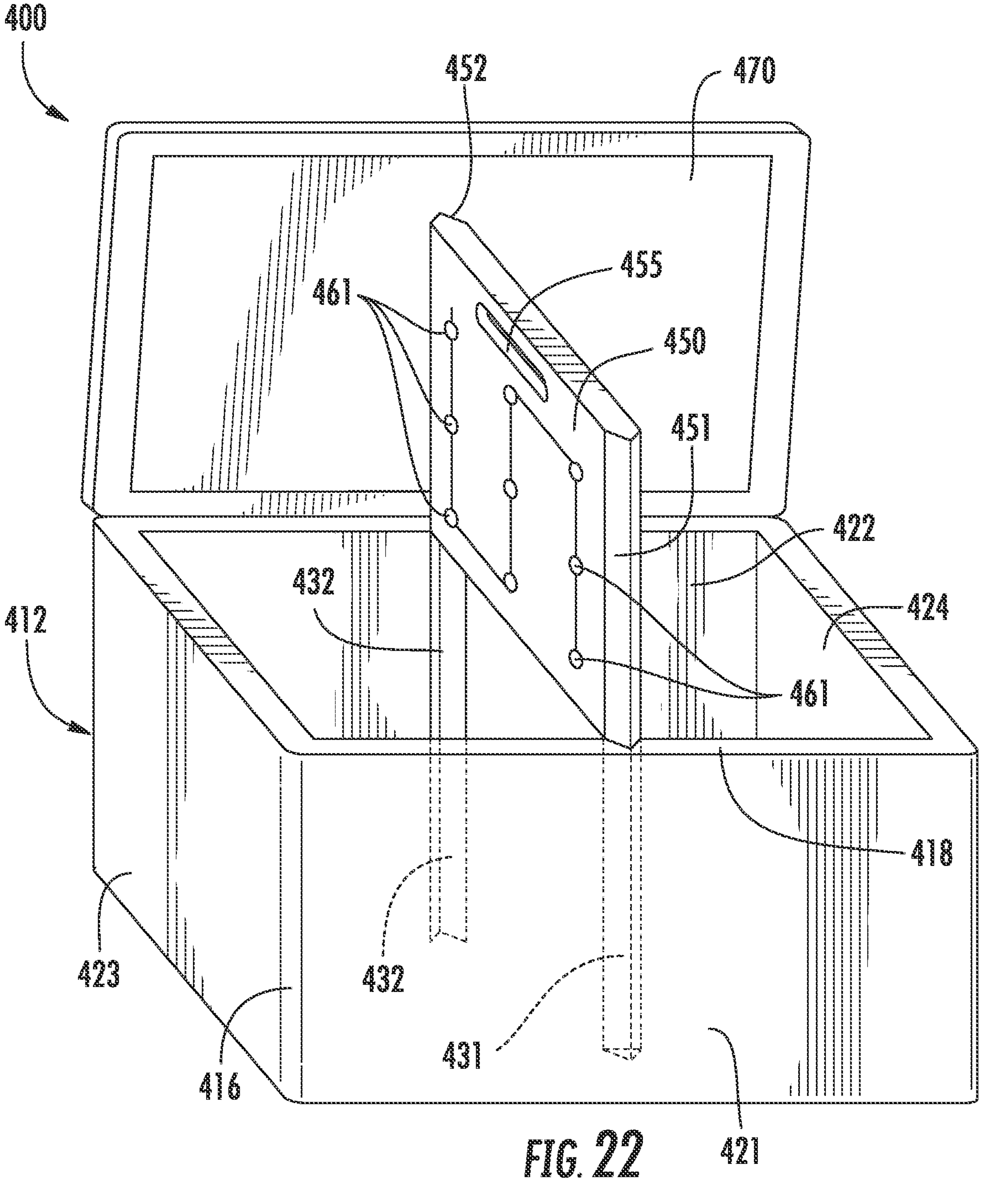
FIG. 22 is a perspective view of a container apparatus according to another preferred embodiment of the invention.
Figure 23:
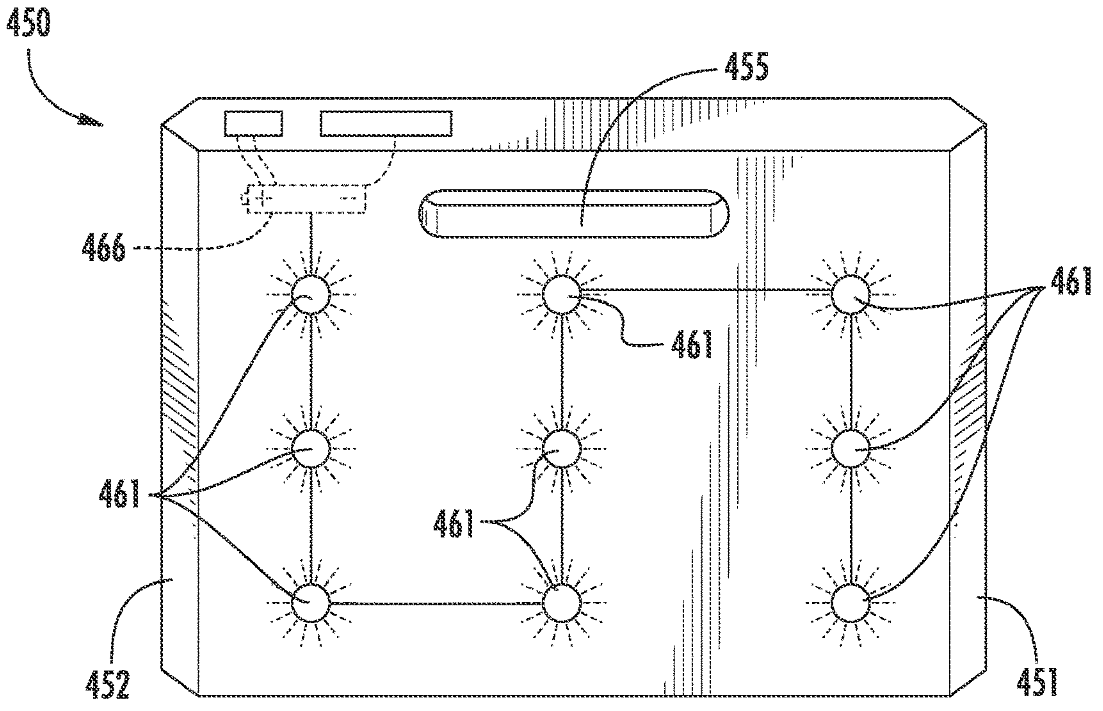
FIG. 23 is a front elevation view of a light assembly insert according to anther preferred embodiment of the invention.
Figure 24:
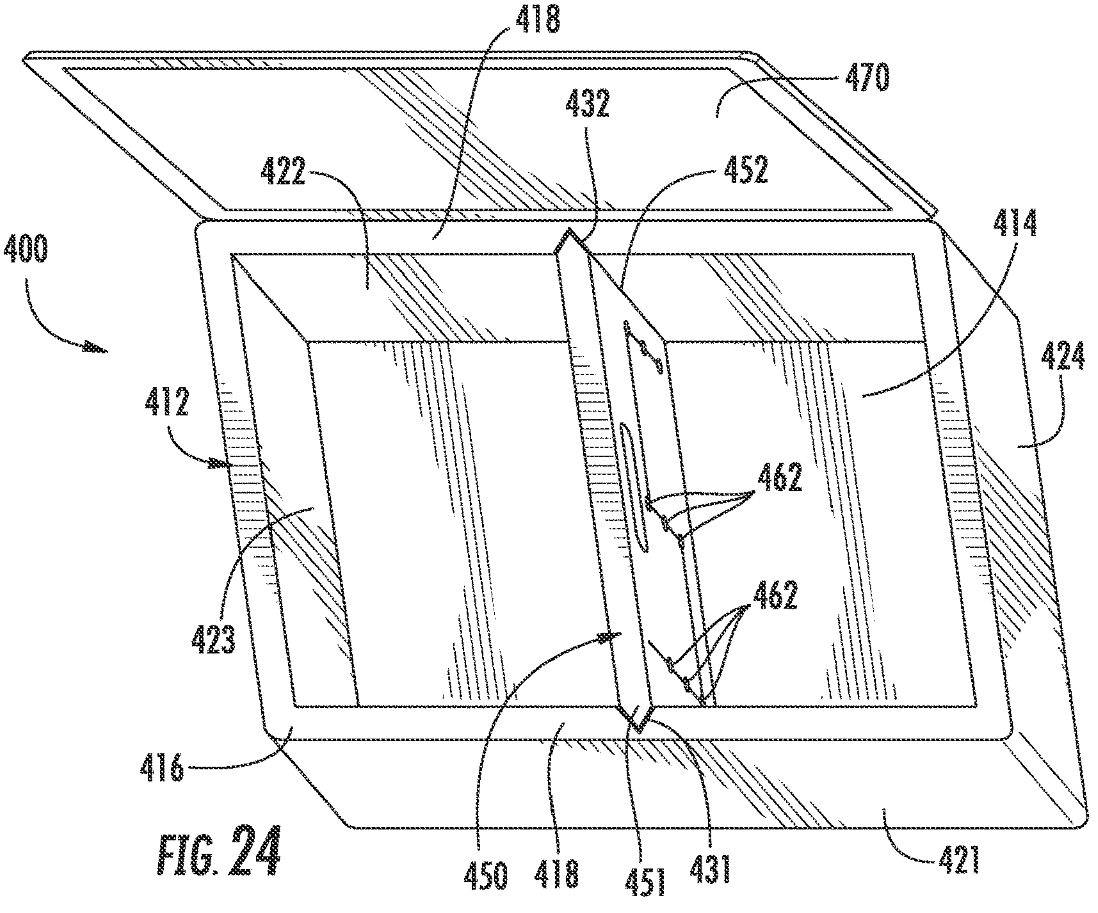
FIG. 24 is a top perspective view of the container apparatus of FIG. 22.

A container apparatus according to another preferred embodiment of the invention is illustrated in FIGS. 22-24 and shown generally at reference numeral 400. The apparatus 400 comprises a container body 412, and a light assembly insert 450. A lid 470 can be connected to the container body 412. The container body 412 and the lid 470 can be made of plastic or other suitable material and can be made by injection molding or other suitable manufacturing process.

The container body 412 comprises a substantially rectangular base 414 for positioning substantially horizontally on a floor surface, and a substantially rectangular sidewall 416 extending substantially vertically from the base 414. The sidewall 416 has four sides 421, 422, 423, 424. Two substantially concave and elongate recesses 431, 432 are formed in the interior surface on opposing sides 401, 402 of the sidewall 416, as shown in FIG. 22. The recesses 431, 432 define channels beginning at the top edge 418 of the sidewall 416 and extending downwardly to the base 414 of the container 412, as shown in FIG. 22. The channels 431, 432 extend substantially vertically, and are substantially perpendicular to the container base 414.

As shown in FIGS. 22-24, the insert 450 comprises a substantially flat and rectangular member having a first group of light emitting devices 461 positioned on one side of the insert 450, and a second group of light emitting devices 462 positioned on the opposite side of the insert 450. The light emitting devices can comprise light emitting diodes (LED), a low-voltage incandescent light bulb, illuminated fiber optic cables, or other suitable light emitting devices. A power source such as a battery 466 can be positioned within the insert 450 and operatively connected to the light emitting devices 461, 462.

The recessed channels 431, 432 are shaped and sized to receive and conform to the side edges 451, 452 of the light assembly insert 450 and are positioned in opposed complementary alignment, as shown in FIGS. 22 and 24, such that the side edges 451, 452 can slide up and down within the channels 431, 432. As shown in FIG. 22, the insert side edges 451, 452 and the recessed channels 431, 432 can have a substantial arrowhead shape. The insert 450 can include an opening 455 formed therein through which the user can grasp the light assembly 450. Alternatively, the insert 450 can include a temperature altering element, such as a refrigerant gel. The refrigerant gel can be a gel formulation comprised of propylene glycol and water or other suitable materials.

When the user wishes to illuminate the interior of the container body 412, the insert 450 is slid down the recessed channels 431, 432 until the bottom edge of the insert 450 rests on the base 414 of the container body 412. The insert 450 is retained in an upright position within the channels 431, 432, as shown in FIG. 24. As such, the light emitting devices 461, 462 of the insert 450 can illuminate the interior of the container body 412. In addition, the insert 450 acts as a divider that separates the interior of the container body 412 into two separate sections, as shown in FIG. 24. When desired, the insert 450 can be easily removed by grasping through the opening 455 and lifting the insert 450 upwardly out of the recessed channels 431, 432.

It is to be noted that while the container apparatus 400 is described and shown in the drawings as having a substantially rectangular container body 412, the invention is not so limited. Alternatively, the container body 412 can be a variety of shapes, such as substantially circular, oval and square.

Figure 25:
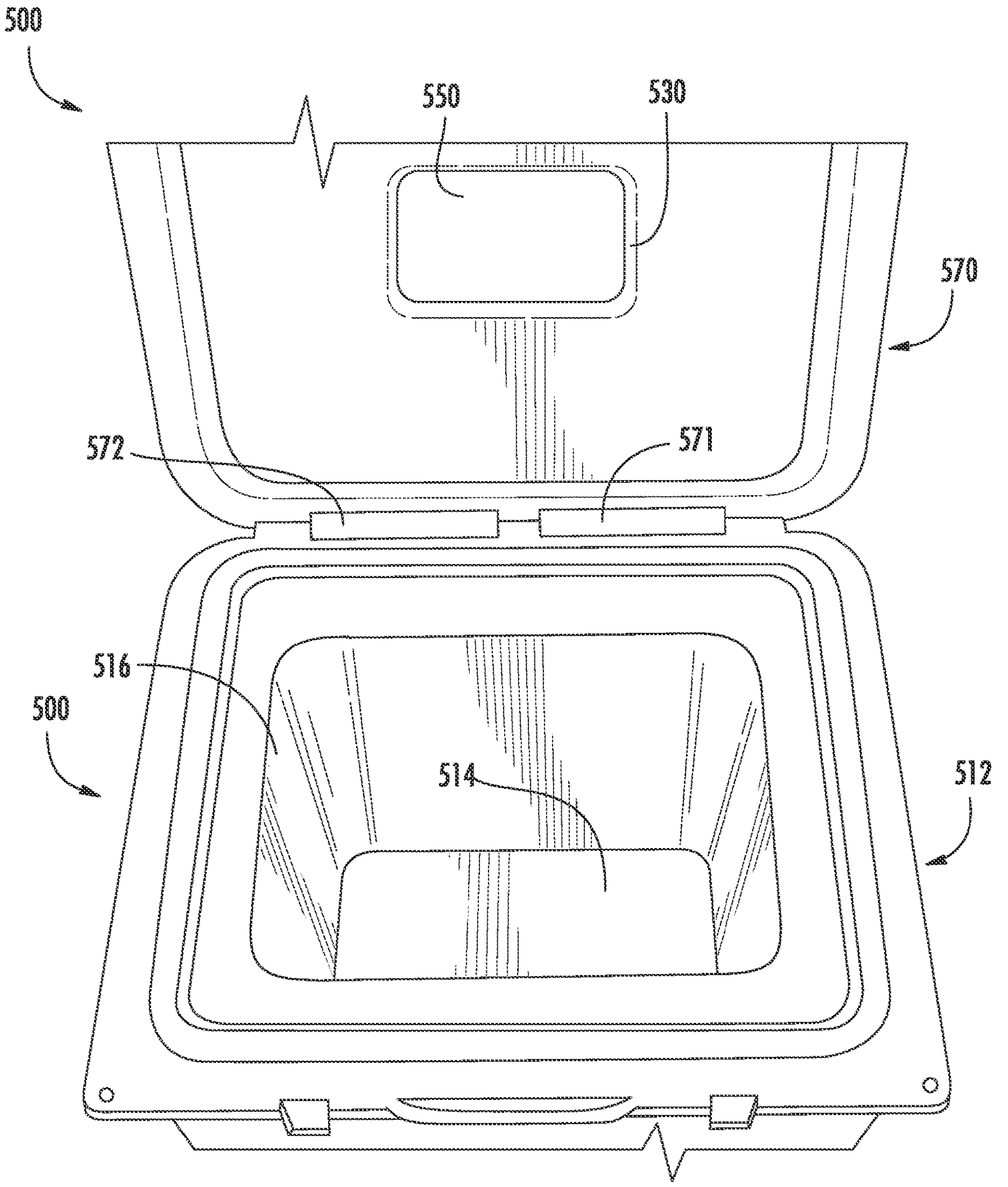
FIG. 25 is a perspective view of a container apparatus according to another preferred embodiment of the invention.

A container apparatus according to another preferred embodiment of the invention is illustrated in FIG. 25, and shown generally at reference numeral 500. As shown in FIG. 25, the apparatus 500 comprises a substantially rectangular body section 512, a lid section 570 connected to the body 512, and an insert assembly 550. The body 512 comprises a substantially rectangular base 514 and a substantially rectangular sidewall 516 extending upwardly from the base. The lid 570 can be pivotally attached to the sidewall 516 of the body 512 by hinges 571, 572. The body 512 and the lid 570 define an enclosure in which items such as food and beverages can be stored. The apparatus 500 can be made of plastic or other material suitable for a thermally insulated cooler.

The insert assembly 550 can be positioned within a substantially concave recess 530 formed in the interior surface of the lid 570, as shown in FIG. 25. The recess 530 is sized and shaped to conform to the size and shape of the light assembly 550 so as to receive and retain the light assembly 550 therein by frictional engagement. Alternatively, the insert assembly 550 can be held within the recess 530 by other attachment means, such as suction cups or adhesive. As shown in FIG. 25, the insert assembly 550 and the recess 530 can be substantially rectangular. Alternatively, the insert assembly 550 and the recess 530 can be other shapes, such as circular or oval.

The insert assembly 550 can comprise at least one light emitting device, such as a light emitting diode (LED), a low-voltage incandescent light bulb, illuminated fiber optic cables, or other suitable light emitting device. Whenever it is desired to illuminate the interior of the container 500, the insert assembly 550 can be positioned within the recess 530 and the light emitting device turned on. Alternatively, the insert assembly 550 can include a battery powered cooling or heating element. In another alternative embodiment, the insert assembly 550 can be comprised of an audio speaker unit, such as a wireless audio speaker having wireless communications technology sold under the mark "BLUETOOTH". In yet another alternative embodiment, the insert assembly 550 can be a dry box container for holding personal items, such as keys, wallets and the like. The container can be made of rubber, plastic or other suitable material.

Figure 26:
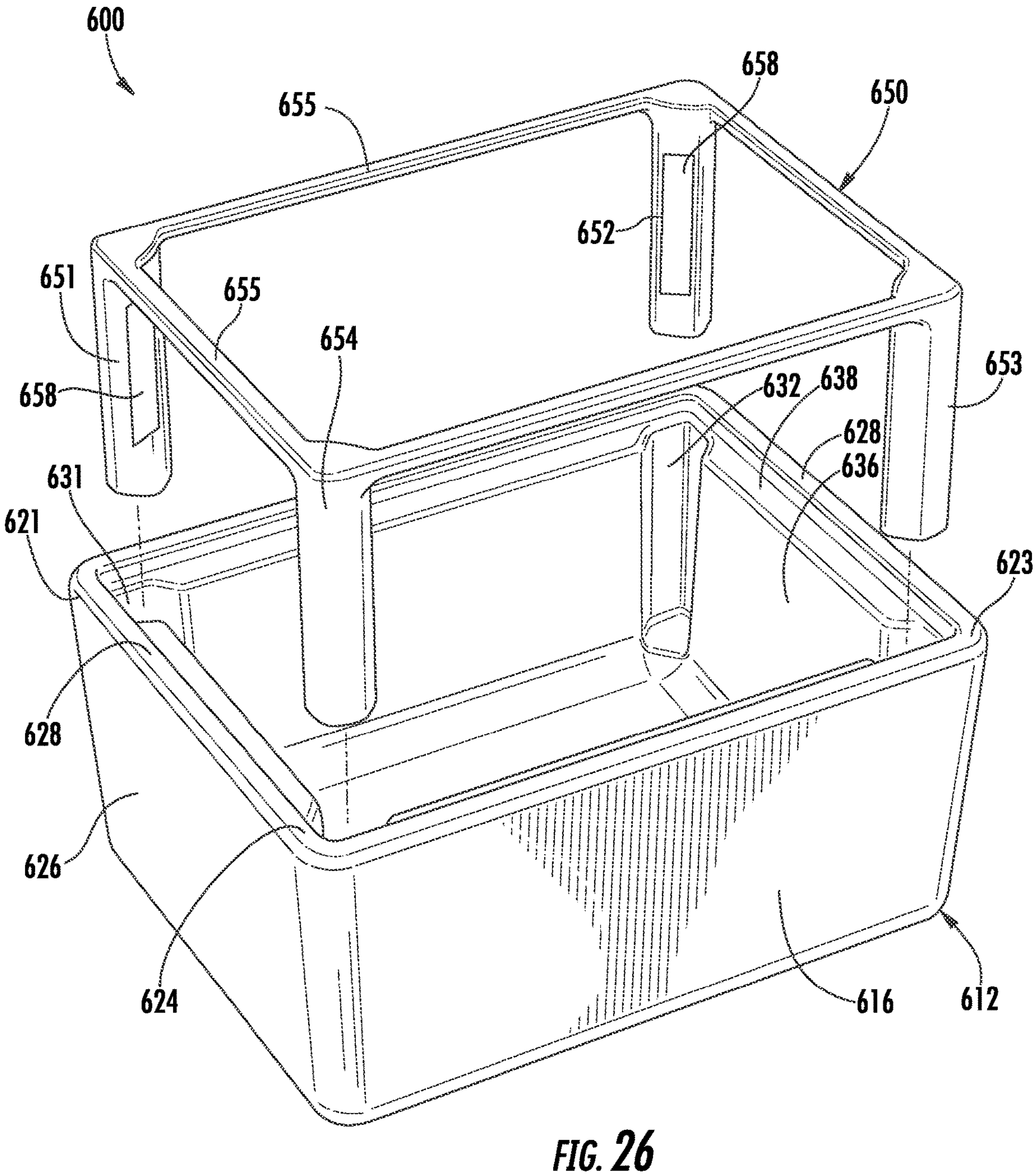
FIG. 26 is a perspective view of a container apparatus according to another preferred embodiment of the invention.
Figure 27:
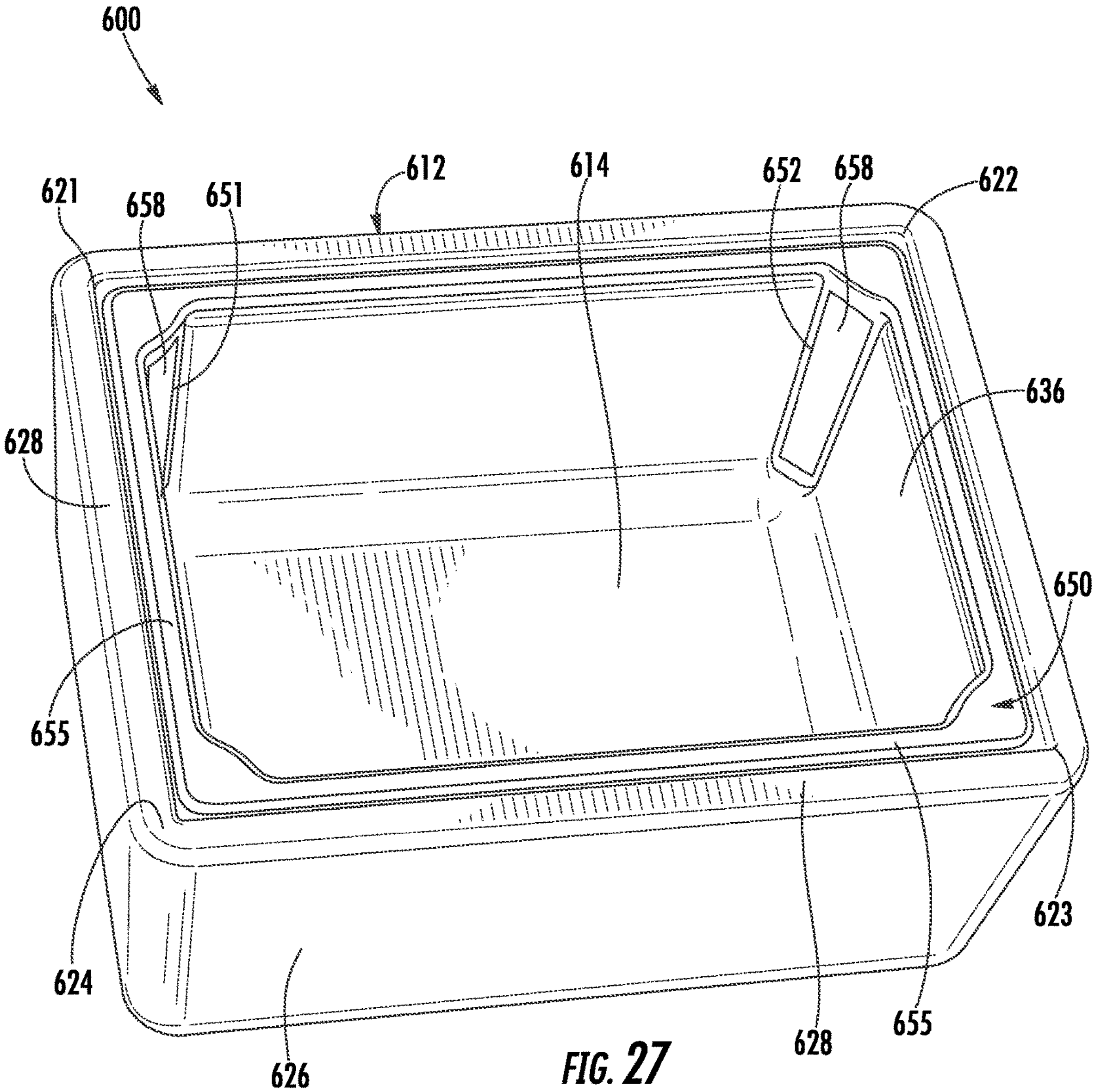
FIG. 27 is another perspective view of the container apparatus of FIG. 26.
Figure 28:
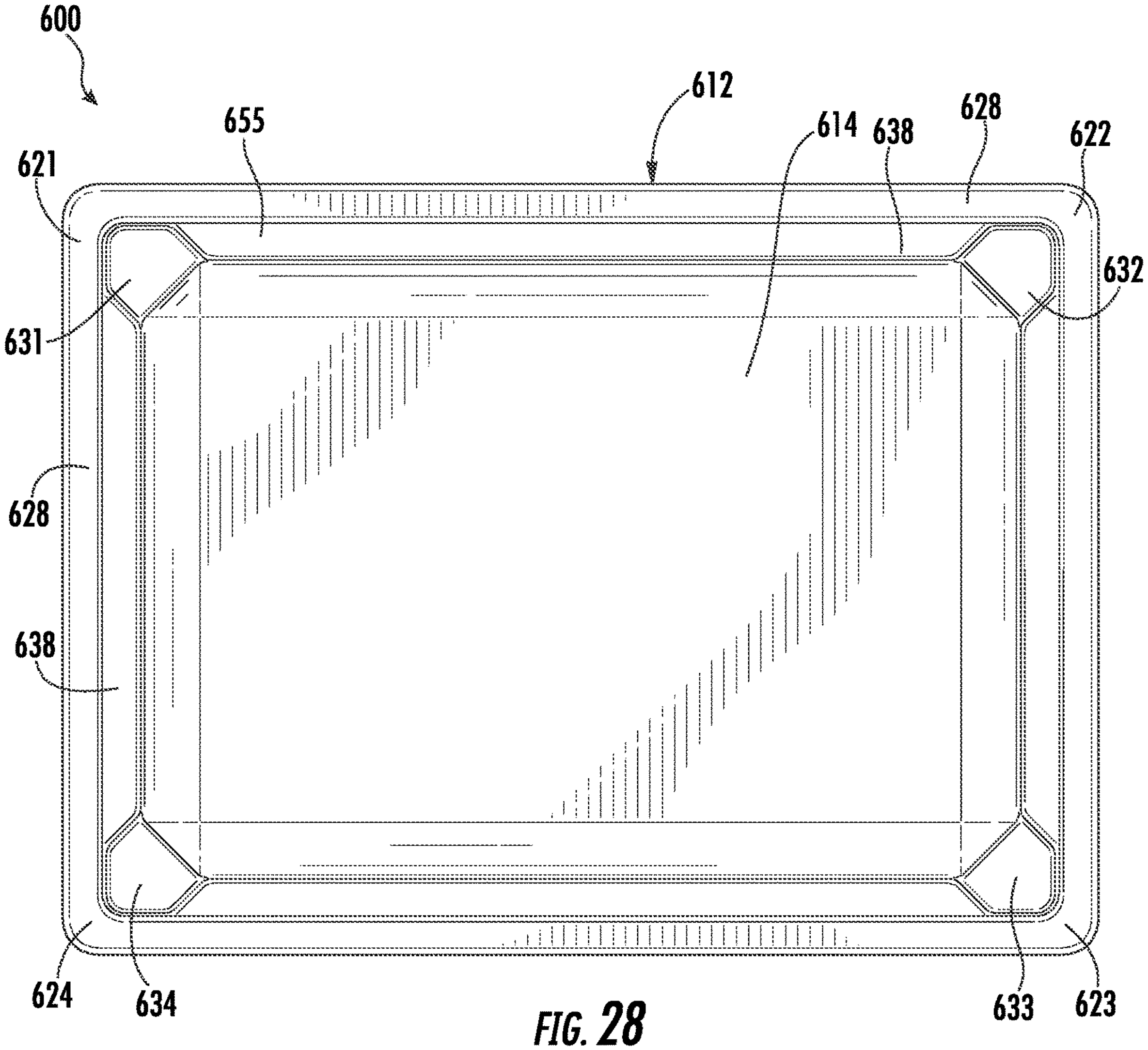
FIG. 28 is a top plan view of the container apparatus of FIG. 26; [woo]

A container apparatus according to another preferred embodiment of the invention is illustrated in FIGS. 26-28 and shown generally at reference numeral 600. As shown in FIG. 26, the apparatus 600 comprises a container 612 and a light assembly insert 650. The word "container" as used herein refers generally to any kind of enclosure. For example, the apparatus 600 can comprise a thermally insulated cooler adapted for storing food and beverages. Alternatively, the container 600 can comprise a toolbox for storing tools, or other type of enclosure.

As shown in FIGS. 26-28, the container 612 comprises a substantially rectangular base 614, and a substantially rectangular sidewall 616 extending upwardly from the base 614. The sidewall 616 has four sides defining four corners 621, 622, 623, 624. The sidewall 616 is comprised of an outer wall section 626 and an inner wall section 636, as shown in FIGS. 26 and 27. The surface of the inner wall section 636 defines an interior surface of the container 612. The top 638 of the inner wall section 636 is lower than the top 628 of the outer wall section 626, thereby creating a tiered rest platform 638, as shown in FIG. 26. The container 612 can be made of plastic or other suitable material and can be made by injection molding or other suitable manufacturing process. It is to be noted that while container apparatus 610 comprises a substantially rectangular container 612, the invention is not so limited. Alternatively, the container 612 can be a variety of shapes, such as substantially circular, oval and square.

Four substantially concave and elongate recesses 631, 632, 633, 634 are formed in the inner wall section 636 proximate the four corners 621, 622, 623, 624, respectively, of the sidewall 616, as shown in FIG. 26. The recesses 631, 632, 633, 634 begin at the top 638 of the inner wall section 636 and extend downwardly to the base 614 of the container 612, as shown at reference numeral 632 in FIG. 26. The recesses 631, 632, 633, 634 can have a substantially pentagonal shape, as shown in FIG. 28.

The light assembly 650 comprises four elongate light members 651, 652, 653, 654 attached to a rectangular top frame 655, as shown in FIG. 26. Each of the four light members 651 are attached at one of the four corners of the rectangular frame 655 and extend downwardly from the rectangular frame member at an angle of about ninety degrees, as shown in FIG. 26.

The elongate recesses 631, 632, 633, 634 in the container 612 are sized and shaped to conform to the elongate light members 651, 652, 653, 654, in order to receive and retain the light members 651, 652, 653, 654 therein. Accordingly, light members 651, 652, 653, 654 have a length approximately equal to the length of the recesses 631, 632, 633, 634 extending from the top 638 of the inner wall section 636 to the base 614, and have a perimeter slightly less than the effective perimeter of the recesses 631, 632, 633, 634, such that the light members 651, 652, 653, 654 can be inserted into the recesses 631, 632, 633, 634, as shown in FIGS. 26 and 27, and retained within the recesses 631, 632, 633, 634 by frictional engagement.

The rectangular frame 655 of the light assembly 650 has a perimeter approximately equal to the perimeter of the rectangular rest platform 638. As such, the frame 655 rests on the rest platform 638 of the inner wall section 636 when the light members 651, 652, 653, 654 are fully inserted into the recesses 631, 632, 633, 634, as shown in FIG. 27. The frame 655 has a height approximately equal to the difference in height between the top edge 628 of the outer wall section 626 and the top edge 638 of the inner wall section 636, such that the top of the frame 655 sits flush with the top 628 of the outer wall section 626 when the light members 651, 652, 653, 654 are fully inserted into the recesses 631, 632, 633, 634, as shown in FIG. 27.

Alternative embodiments can utilize an additional engagement mechanism for facilitating retention of the light members 651, 652, 653, 654 within the recesses 631, 632, 633, 634. For example, a plurality of protuberances can be positioned on the outer surface of the light members 651, 652, 653, 654 to engage a plurality of corresponding openings formed on the portion of the inner wall section 636 defining the recesses 631, 632, 633, 634 when the light members 651, 652, 653, 654 are fully inserted into the recesses 631, 632, 633, 634. The protuberances residing within the openings further retain the light members 651, 652, 653, 654 within the recesses 631, 632, 633, 634. Alternatively, a plurality of protuberances can be formed on the portion of the inner wall section 636 defining the recesses 631, 632, 633, 634 to engage a plurality of corresponding apertures formed in the light members 651, 652, 653, 654 when the light members 651, 652, 653, 654 are inserted into the recesses 631, 632, 633, 634.

Each elongate light member 651, 652, 653, 654 is comprised of a housing containing a light emitting device, such as a light emitting diode (LED), a low-voltage incandescent light bulb, illuminated fiber optic cables, or other suitable light emitting device. As such, whenever it is desired to emit light into the interior of the container 612, the light assembly 650 is positioned within the container 612 by inserting the light members 651, 652, 653, 654 into the recesses 631, 632, 633, 634, as shown in FIGS. 26 and 27, and turning on the light emitting devices of the light members 651, 652, 653, 654.

Each elongate light member 651, 652, 653, 654 can comprise a germicidal light emitting device, such as an ultraviolet light. Preferably, each light member 651, 652, 653, 654 comprises an ultraviolet light that emits light having a wavelength of one hundred nanometers to two hundred ninety nanometers (UV-C). The light members 651, 652, 653, 654 emit UV-C light that can inactivate various microbes, such as viruses, including corona viruses, bacteria, molds and other pathogens. The light members 651, 652, 653, 654 emit UV-C light that deactivates the DNA of viruses, bacteria and other pathogens, thereby destroying their ability to multiply and cause disease. In addition, the UV-C light emitted by the light members 651, 652, 653, 654 helps to keep food in the container 612 fresh by destroying bacteria, and helps prevent foul odors from developing in the container 612 by destroying odor causing microbes.

Each light member 651, 652, 653, 654 can comprise a housing that includes a translucent lens section 658 positioned in front of the ultraviolet light that is adapted to lower the wavelength of the light emitted from the ultraviolet light. The lens 658 can be frosted, glazed, tinted and/or etched. In a preferred embodiment, each light member 651, 652, 653, 654 includes an ultraviolet light that emits light at a wavelength of 250-290 nanometers (nm), and when the light contacts the lens 658, the wavelength of the light is reduced to 220-249 nm, which is the optimum wavelength range for effectively deactivating viruses, bacteria, molds and other pathogens while minimizing harm caused by exposure to humans. As such, the light members 651, 652, 653, 654 enable the delivery of ultraviolet light having a wavelength in an optimum wavelength range of 220-249 nm for safely destroying viruses, bacteria, molds and other pathogens while using lower cost 250-290 wavelength ultraviolet lights. For example, in a particular preferred embodiment, each light member 651, 652, 653, 654 includes an ultraviolet light that emits light at a wavelength of 285 nanometers (nm), which is reduced to 240 nm by the lens 658. U.S. Pat. No. 6,911,657 is incorporated herein by reference.

Preferably, the light emitting device is powered by disposable or rechargeable batteries. The light emitting devices can be set on a timer such that they automatically turn off after a certain period of time to avoid draining of the batteries. The light assembly 650 is not wired to or otherwise electrically connected to the container 612, and no electric wiring is located within the container 612. As such, the light assembly 650 can be easily removed from the container 612 to repair a malfunction in one of the light members 651, 652, 653, 654, or replace drained batteries. Also, the light assembly 650 can be removed when there is no desire for illumination within the container 612 or when it is desired to replace the light assembly 650 with a new unit. Since the light assembly 650 is not operatively connected to or functionally dependent upon the container 612, and can be easily removed from the container 612, the light assembly 650 and container 612 can be manufactured, distributed and/or sold as separate units. Alternatively, the light assembly 650 and container 612 can be distributed and/or sold as components of a container kit.

The container apparatus 600 can include a lid pivotally attached to top of the sidewall 616 of the container 600. An embodiment of the invention comprises a method of disinfecting items using the container apparatus 600. Items to be disinfected are placed within the interior of the container 612. The items can be food, beverages, packages and/or other items. The light assembly 650 is turned on, and the lid is closed. UV-C light is emitted from the light members 651, 652, 653, 654 and deactivates viruses, bacteria, and other pathogens present on the items. The lid can be opened, and the items can be removed from the container 612. In another embodiment, the container apparatus 600 can be used to transport human tissue, such as blood and/or organs. Another embodiment of the invention comprises a method of decontaminating liquid. A liquid, such as water, is placed within the container 612, and the UV-C light members 651, 652, 653, 654 are activated to destroy harmful microbes present in the water.

According to a preferred embodiment of the invention, some of the light members emit germicidal ultraviolet light, while other light members can comprise light emitting devices that emit light that is visible to the human eye. For example, light members 651, 653 can be adapted to emit ultraviolet light at a wavelength of about 220-249 nanometers, and light members 652, 654 can be adapted to emit light having a wavelength of about 380-740 nanometers. As such, light members 651, 653 deactivate viruses, bacteria and other microbes within the container 612, while light members 652, 654 light up the interior of the container 612 and assist the user in seeing items inside the container.

Figure 29:
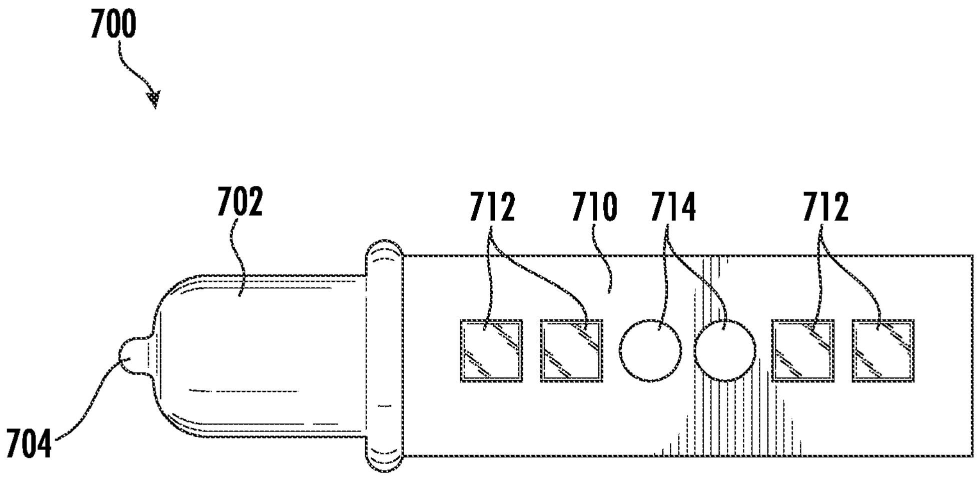
FIG. 29 is a side elevation of a light apparatus according to another preferred embodiment of the invention.

An appliance light apparatus according to another embodiment of the invention is illustrated in FIG. 29 and shown generally at reference numeral 700. The light apparatus is adapted for use in an appliance, such as a refrigerator or freezer. The apparatus 700 can replace a conventional refrigerator light, such as the light devices described in U.S. Pat. No. 7,275,381, which is incorporated herein by reference.

The apparatus 700 comprises a base 702 and a light section 710. The base 702 has screw threads and an electrical foot contact 704 for engaging an electrical socket, such as the socket for a conventional refrigerator light. The light section 710 section includes a plurality of ultraviolet lights 712 emitting UV-C light and a plurality of lights 714 emitting light visible to the human eye (referred to herein as "visible lights"). The lights 712, 714 are electrically connected to the foot contact 704. Preferably, the lights 712, 714 are light emitting diodes (LEDs).

The lights 712, 714 are powered by a rechargeable battery in the light section 710. The base 702 can be threadingly engaged within the light socket of a refrigerator, and when the base 702 is positioned within the refrigerator light socket, the foot contact 704 electrically connects to the socket. The apparatus 700 is wired such that when the refrigerator door opens, the visible lights 714 turn on, and the battery in the light section 710 is recharged.

The apparatus 700 includes sensor means for turning off the UV-C lights 712 when the refrigerator door is opened and turning the UV-C lights 712 on when the door is closed. The apparatus 700 can include a motion sensor positioned in the light section 710 and operatively connected to UV-C lights 712 so that when the motion sensor detects the motion of the refrigerator door opening, the UV-C lights 712 are turned off. When the motion sensor detects motion for a second time (the refrigerator door closing) the UV-C lights 712 are turned on. In an alternative embodiment, the apparatus 700 can include an optic sensor positioned in the light section 710 and operatively connected to the UV-C lights such that the UV-C lights 712 turn off when the optic sensor senses light from the refrigerator door being opened, and turns on when the optic sensor no longer detects light (due to the refrigerator door being closed.) In another embodiment, the apparatus 700 can include a temperature sensor positioned in the light section 710 and operatively connected to the UV-C lights 712 such that the UV-C lights 712 turn off when the sensor detects an increase in the temperature within the refrigerator (due to the refrigerator door opening) from a predetermined set temperature for the refrigerator, and the UV-C lights 712 turn on when the sensor detects the temperature within the refrigerator has returned to the predetermined set temperature (due to the refrigerator door being closed). In yet another embodiment, the sensor means can comprise a photoelectric sensor.

When the refrigerator door is closed, the UV-C lights 712 come on and remain on for a predetermined amount of time or until the refrigerator door is opened again, whichever happens first. The light section 710 can include a timer operatively connected to the UV-C lights 712 so that they cut off after a predetermined amount of time, such as one to two minutes.

The visible lights 714 of the apparatus 700 provide visible light within the refrigerator when the refrigerator door is open, as does a conventional refrigerator light, and when the door is closed the UV-C lights 712 emit UV-C light that destroys various microbes, such as viruses, including corona viruses, bacteria, molds and other pathogens. In addition, the UV-C lights 712 help keep food and beverages in the refrigerator fresh by destroying bacteria and mold and helps prevent foul odors from developing in the refrigerator by destroying odor causing microbes. The apparatus 700 allows the user to increase the set temperature of the user's refrigerator, because the apparatus 700 helps preserve food in the refrigerator by destroying mold and bacteria.

In a preferred embodiment, the UV-C lights 712 emit ultra-violet light having a wavelength in the range of 220-249 nm. In an alternative embodiment, the UV-C lights emit ultra-violet light having a wavelength in the range of 250-290 nm, and the apparatus 700 includes a lens covering each of the UV-C lights 712 adapted to reduce the wavelength of the light from 250-290 nm to 220-249 nm. The lens can be glazed, frosted, tinted and/or etched.

In another embodiment, the light section includes a mother board comprising a computing device, such as a microcontroller. The motherboard is operatively connected to the lights 712, 714 and can control the wattage delivered to the lights 712, 714. In this embodiment, each of the UV-C lights 712 can be one-watt lights that emit light having a wavelength in the range of 250-290 nm. The microcontroller reduces the wattage delivered to the UV-C lights 712 from one watt to 0.5 watt, thereby making the light emitted by the UV-C lights 712 safer for human exposure.

Figure 30:
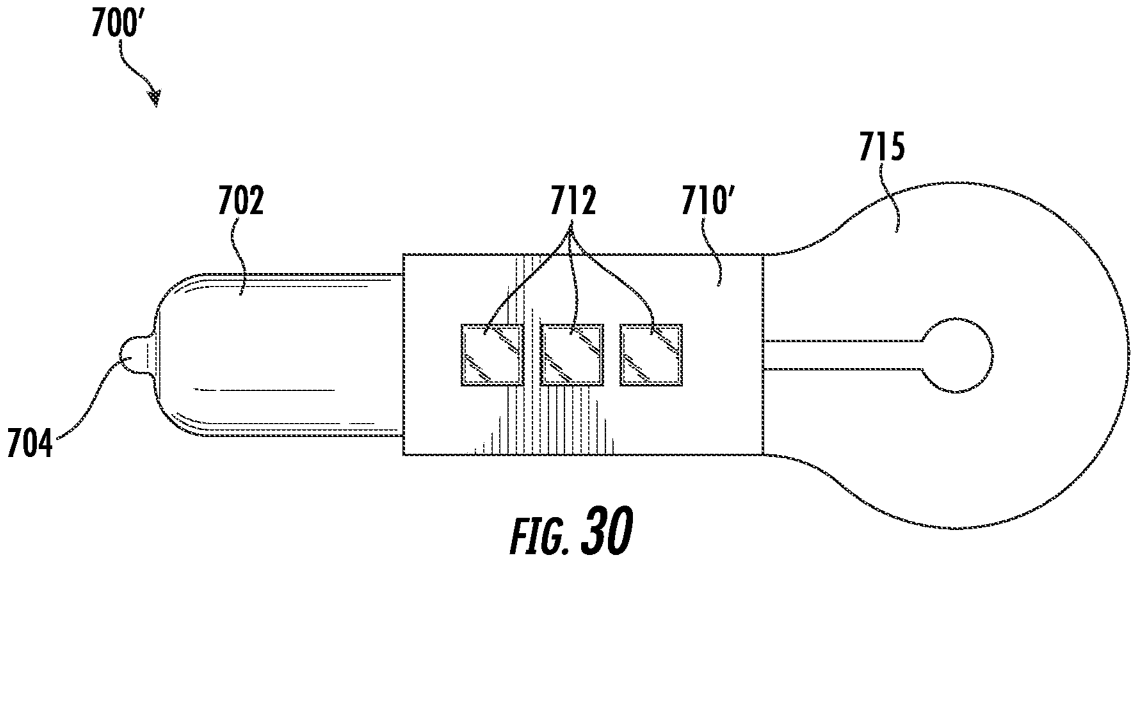
FIG. 30 is a side elevation of a light apparatus according to another preferred embodiment of the invention.

A light apparatus according to another embodiment of the invention is illustrated in FIG. 30 and shown generally at reference numeral 700'. The light apparatus 700' comprises a base 702 with screw threads and an electrical foot contact 704 for engaging an electrical socket, such as the socket for a conventional refrigerator light, and a light section 710' section that includes a plurality of ultraviolet UV-C lights 712. An incandescent light bulb 115 that emits light visible to the human eye is connected to the light section 710'.

Figure 31:
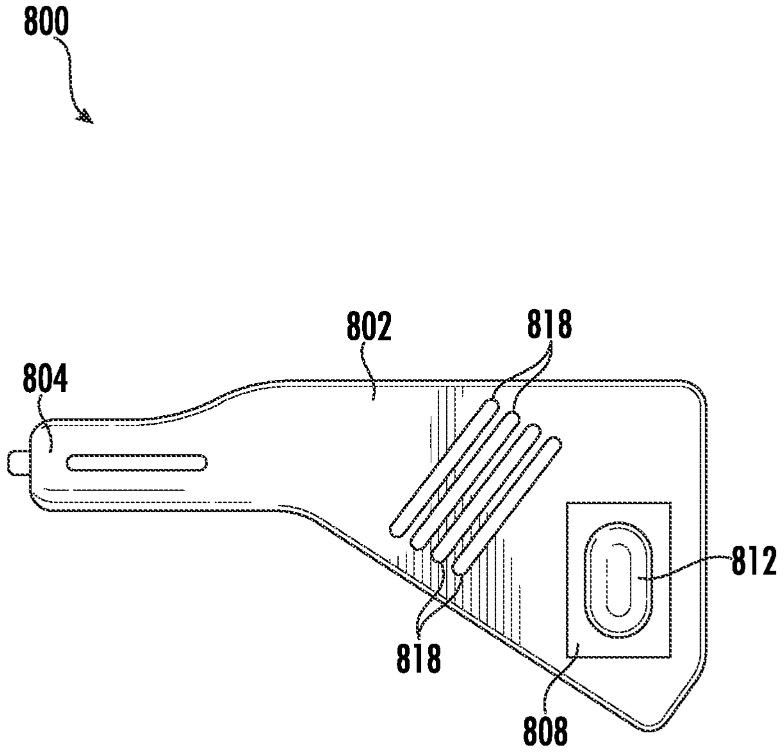
FIG. 31 is a side elevation of a light apparatus according to another preferred embodiment of the invention.
Figure 32:
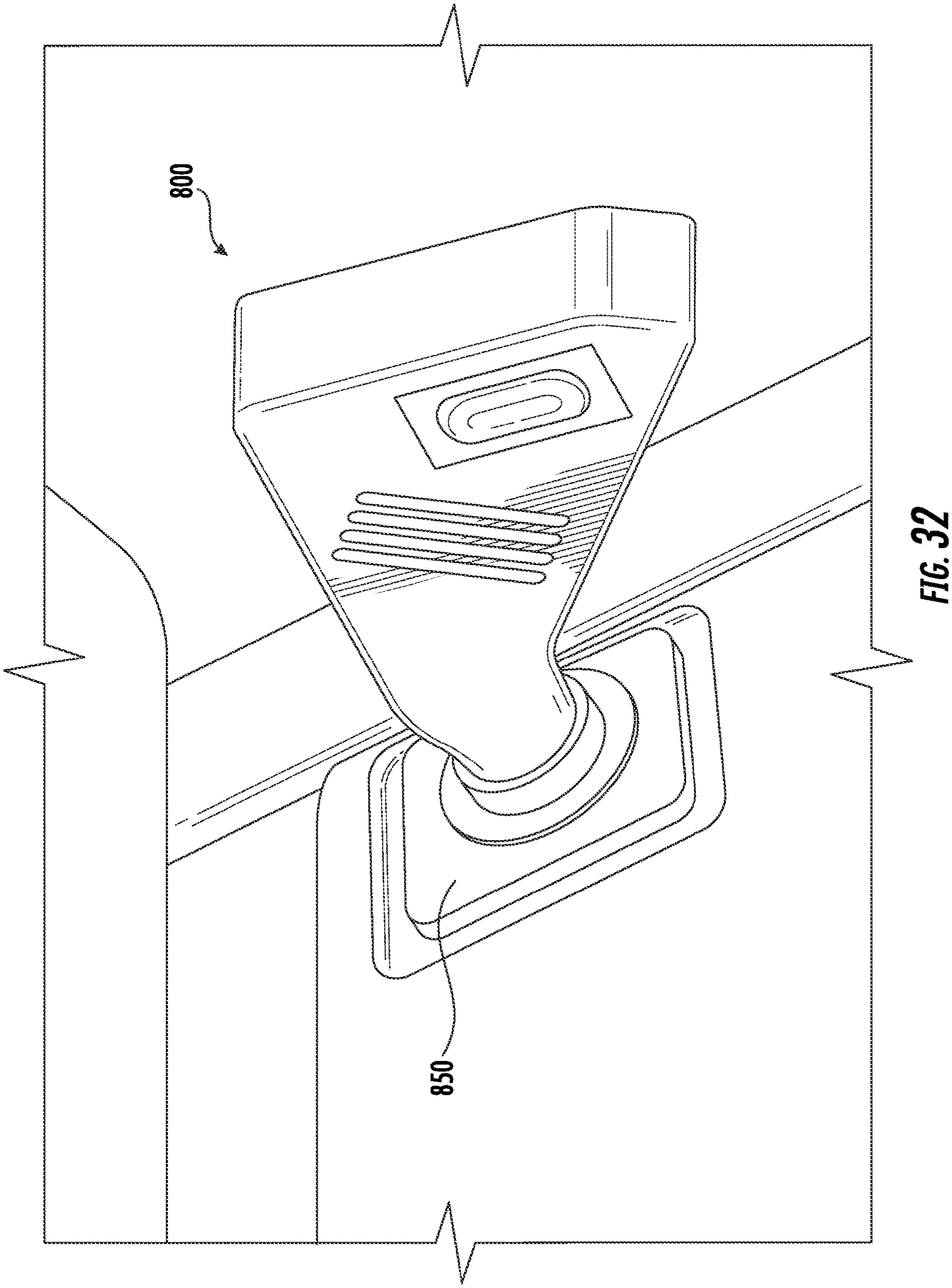
FIG. 32 is a perspective view of the light apparatus of FIG. 31.

A sanitizing ultraviolet light apparatus according to another embodiment of the invention is illustrated in FIG. 31 and shown generally at reference numeral 200. The apparatus 800 is adapted for use in an auxiliary power outlet. The apparatus 800 comprises a housing 802 comprising a male plug 804 adapted for being plugged into and engaging the socket of an auxiliary power outlet, such as an automobile auxiliary power outlet 850 (also known as the automobile's cigarette lighter), as shown in FIG. 32. A UV-C light 812 is positioned in the housing 802 and is operatively connected to the male plug 804. Preferably, the UV-C light 812 is a light emitting diode (LED).

As shown in FIG. 32, the apparatus 800 can be electrically connected to the socket of an automobile auxiliary power outlet 850 and used to sanitize air within the automobile. The apparatus 800 can comprise a power supply circuit, such as described in U.S. Pat. No. 6,917,502, which is incorporated herein by reference. The UV-C light 812 emits UV-C light that destroys various microbes, such as viruses, including corona viruses, bacteria, molds and other pathogens within the interior of the automobile.

The UV-C light 812 emits ultra-violet light having a wavelength in the range of 100-280 nm. In a preferred embodiment, the UV-C lights 812 emits ultra-violet light having a wavelength in the range of 220-249 nm. Alternatively, the UV-C light 812 emits ultra-violet light having a wavelength in the range of 250-290 nm, and the housing 802 includes a lens 808 covering the UV-C light 812 that reduces the wavelength of the light emitted from the apparatus 800 from 250-290 nm to 220-249 nm. The lens 808 can be glazed, frosted, tinted and/or etched to reduce the wavelength of the light emitted from the apparatus 800 from 250-290 nm to 220-249 nm. Ultra-violet light having a wavelength of 220-249 nm is safer for human exposure than ultra-violet light in the wavelength range of 250-290 nm.

In another embodiment, a mother board comprising a computing device, such as a microcontroller is positioned within housing 802. The motherboard is operatively connected to the light 812 and can control the wattage delivered to the UV-C light 812. In this embodiment, the UV-C light 812 can be a one-watt light that emits light having a wavelength in the range of 250-290 nm. The microcontroller reduces the wattage delivered to the UV-C light 812 from one watt to 0.5 watt, thereby making the light emitted by the UV-C light 812 safer for human exposure.

A scented wafer, such as the scented wafer described in U.S. Pat. No. 10,245,343, which is incorporated by reference herein, can be positioned within the housing 802. The scented wafer can be adapted to release a scent when exposed to heat at a predetermined temperature. The scented wafer can be positioned in the housing 802 and electrically connected to the male plug 804 such that the scented wafer is heated when the plug 804 engages the electric socket of a power outlet. The heated scented wafer releases a distinct pleasant scent that emanates through a plurality of vents 818 formed in the housing 802. The apparatus 800 can include a micro-fan positioned within the housing 802 that draws air into the housing 802 from the interior of the automobile and blows scented air out of the housing 802 through the vents 818.

Figure 33:
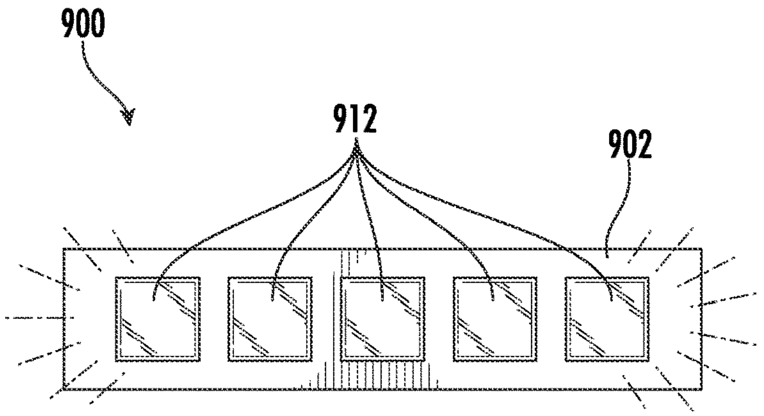
FIG. 33 is a front elevation of a light apparatus according to another preferred embodiment of the invention.
Figure 34:
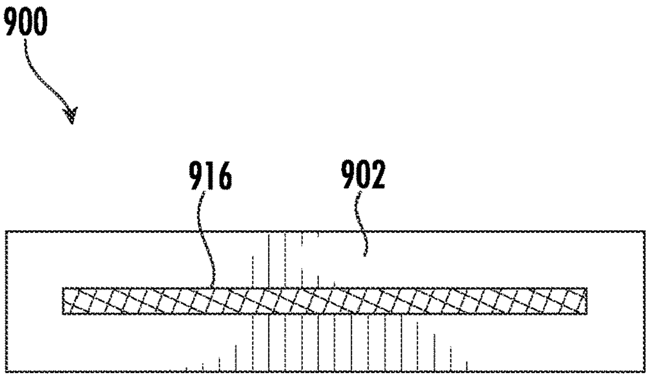
FIG. 34 is a rear elevation of the light apparatus of FIG. 33.
Figure 35:
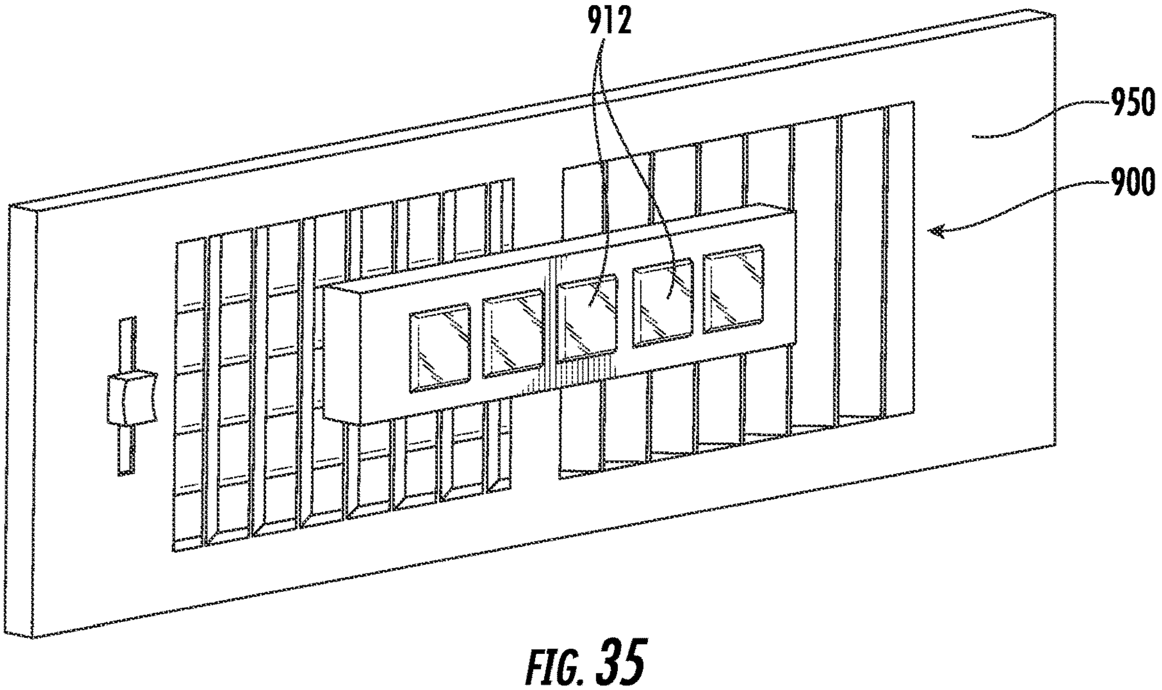
FIG. 35 is a perspective environmental view of the light apparatus of FIG. 33.

A sanitizing ultraviolet light apparatus according to another embodiment of the invention is illustrated in FIGS. 33-35 and shown generally at reference numeral 900. The apparatus 900 comprises a housing 902, and a plurality of ultraviolet lights 912 emitting UV-C light (wavelength of 100 to 280 nm) are positioned on the front side of the housing 902, shown in FIG. 33.

A magnetic member 916 is positioned on the back side of the housing 902, shown in FIG. 34. The magnetic member 916 is comprised of a material having magnetic properties. Preferably, the magnetic member 916 comprises a magnet made of ceramic ferrite or samarium cobalt. As such, the apparatus 900 can be magnetically attached to a metal surface by positioning the magnet 916 against the metal surface. As shown in FIG. 35, the apparatus 900 can be attached to a metal HVAC air vent 950, and the apparatus 900 can sanitize air flowing through the vent.

The UV-C lights 912 can be powered by a rechargeable battery positioned in the housing 902. The apparatus 900 can include a USB port in the housing 902 to receive a USB cord to recharge the battery.

The apparatus 900 can include sensor means for turning the UV-C lights 912 on when air is flowing through the vent and turning the UV-C lights 912 off when air is not flowing. The apparatus 900 can include a small flag or similar lightweight item attached to the housing, and a motion sensor or photoelectric sensor positioned in the housing and operatively connected to UV-C lights 912. When air flows through the vent it moves the flag, the movement is detected by the sensor, and a signal is sent to the UV-C lights 912 that turns the UV-C lights 912 on. When air flow stops the flag does not move, and when the sensor no longer detects motion a signal is sent to the UV-C lights 912 to turn the lights 912 off. In an another embodiment, the apparatus 900 can include a temperature sensor positioned in the housing 902 and operatively connected to the UV-C lights 912 such that the UV-C lights 912 turn on when the sensor detects the temperature is above or below the temperature set on the HVAC thermostat associated with the vent to which the apparatus 900 is attached, and the UV-C lights 912 turn off when the sensor detects the temperature is at the temperature set on the thermostat.

The UV-C lights 912 emit UV-C light that destroys various microbes, such as viruses, including corona viruses, bacteria, molds and other pathogens in the air flowing through the vent. In a preferred embodiment, the UV-C lights 912 emit ultra-violet light having a wavelength in the range of 220-249 nm. In an alternative embodiment, the UV-C lights emit ultra-violet light having a wavelength in the range of 250-290 nm, and the apparatus 900 includes a lens covering each of the UV-C lights 912 adapted to reduce the wavelength of the light from 250-290 nm to 220-249 nm. The lens can be glazed, frosted, tinted and/or etched.

The apparatus 900 can include a mother board comprising a computing device, such as a microcontroller. The motherboard can be operatively connected to the lights 312 and can control the wattage delivered to the lights 912. In this embodiment, each UV-C light 912 can be a one-watt light that emits light having a wavelength in the range of 250-290 nm. The microcontroller can reduce the wattage delivered to the UV-C lights 912 from one watt to 0.5 watt, thereby making the light emitted by the UV-C lights 912 safer for human exposure.

The mother board can be operatively connected to wireless technology, such as the wireless communication technology sold under the mark "BLUETOOTH", so that the apparatus 900 can be operatively connected to a remove device, such as a mobile smartphone. As such, the apparatus 900 can be operated via the remote device.

It should be noted that the invention is not limited to the embodiments described above. In particular, the light assembly of the invention can be a variety of sizes and shapes, and the container can have one or more recesses sized and shaped to compliment the particular size and shape of the light assembly and facilitate insertion of the light assembly into the container. For example, the light assembly can comprise one or more rectangular panels containing light emitting devices that are inserted into one more recesses in the container. Also, while particular embodiments of the invention comprise substantially rectangular containers, the invention is not so limited. Containers of the invention can be a variety of shapes, including substantially square, circular and oval.

A container apparatus and a method of using same are described above. Various changes can be made to the invention without departing from its scope. The above description of preferred embodiments and best mode of the invention are provided for the purpose of illustration only and not limitation—the invention being defined by the claims.

What is claimed is:

1. A container apparatus comprising an enclosure and a light assembly, the enclosure defining an interior area for storing items therein, the enclosure having an interior surface facing the interior area and at least one concave recess formed in the interior surface forming a recessed portion of the interior surface, the at least one concave recess sized and shaped to receive and releasably retain the light assembly therein, wherein the light assembly comprises a light emitting device and is flush with a non-recessed portion of the interior surface when positioned in the at least one concave recess, wherein the light emitting device emits ultraviolet light having a wavelength of 100 to 290 nanometers, and further wherein the light assembly comprises a housing comprising a translucent lens and the light emitting device is positioned within the housing to emit light through the lens, the lens adapted to lower a wavelength of light contacting the lens whereby light emitted from the light emitting device has a first wavelength prior to contacting the lens and the light has a second wavelength lower than the first wavelength after contacting the lens.

2. The container apparatus according to claim 1, wherein the light emitting device comprises a light emitting diode that emits ultraviolet light having a wavelength of about 265 nanometers.

3. The container apparatus according to claim 1, wherein the light emitting device comprises a mercury vapor lamp that emits ultraviolet light having wavelength of about 254 nanometers.

4. The container apparatus according to claim 1, wherein the light emitting device comprises an excimer lamp emitting ultraviolet light having a wavelength of about 222 nanometers.

5. The container apparatus according to claim 1, wherein the first wavelength is in the range of 250 to 290 nanometers, and the second wavelength is in the range of 220-249 nanometers.

6. The container apparatus according to claim 1, wherein the translucent lens is frosted, glazed, tinted or etched.

7. The container apparatus according to claim 1, wherein the light assembly is releasably retained within the at least one concave recess, and the light assembly can be slid in and out of the at least one substantially concave recess.

8. The container apparatus according to claim 1, wherein the light assembly can be removed from the at least one concave recess without removing any other component of the container apparatus.

9. The container apparatus according to claim 1, wherein the light emitting device is not electrically connected to the enclosure.

10. A light apparatus comprising:

(a) a base and a light section, the base comprising an electrical foot contact adapted to engage an electrical socket of a refrigerator; and (b) a light section comprising at least one ultraviolet light emitting device and at least one visible light emitting device electrically connected to the electrical foot contact, and a power source operatively connected to the at least one ultraviolet light emitting device and the at least one visible light emitting device, wherein the light section comprises at least one translucent lens adapted to lower a wavelength of light contacting the lens, wherein light emitted from the at least one light emitting device has a first wavelength prior to contacting the at least one translucent lens and the light has a second wavelength lower than the first wavelength after contacting the at least one translucent lens.

11. The light apparatus according to claim 10, wherein the first wavelength is in the range of 250 to 290 nanometers, and the second wavelength is in the range of 220-249 nanometers.

12. A container apparatus comprising:

(a) an enclosure defining an interior area for storing items therein, the enclosure having an interior surface facing the interior area and at least one recess formed in the interior surface; and (b) a light assembly positioned in the at least one recess, the light assembly comprising a light emitting device and a housing containing the light emitting device, the housing comprising a translucent lens and the light emitting device positioned within the housing to emit light through the translucent lens, wherein the lens is adapted to lower a wavelength of light contacting the lens whereby light emitted from the light emitting device has a first wavelength prior to contacting the lens and the light has a second wavelength lower than the first wavelength after contacting the lens.

13. The container apparatus according to claim 12, wherein the first wavelength is in the range of 250 to 290 nanometers, and the second wavelength is in the range of 220-249 nanometers.

14. The container apparatus according to claim 13, wherein the translucent lens is frosted, glazed, tinted or etched.

15. The container apparatus according to claim 12, wherein the translucent lens is frosted, glazed, tinted or etched.

16. The container apparatus according to claim 12, wherein the light assembly is releasably retained within the at least one recess, and the light assembly can be slid in and out of the at least one recess.

17. The container apparatus according to claim 12, wherein the light assembly can be removed from the at least one recess without removing any other component of the container apparatus.

18. The container apparatus according to claim 12, wherein the light emitting device is not electrically connected to the enclosure.

19. The container apparatus according to claim 12, wherein the enclosure comprises a base, a sidewall extending upwardly from the base, and a lid pivotally attached to a top of the sidewall.

* * * * *